(12) United States Patent
Coombs et al.

(10) Patent No.: US 6,306,618 B1
(45) Date of Patent: Oct. 23, 2001

(54) HOMOCYSTEINE DESULPHURASE FROM THE PROTOZOAN TRICHOMONAS VAGINALIS

(75) Inventors: Graham Herbert Coombs, Glasgow; Jeremy Charles Mottram, Bearsden; David John Pritchard, Scone; Robert Stewart Campbell, Perth, all of (GB)

(73) Assignee: University of the University of Glasgow (GB)

( * ) Notice: Subject to any disclaimer, the term of this patent is extended or adjusted under 35 U.S.C. 154(b) by 0 days.

(21) Appl. No.: 09/242,859

(22) PCT Filed: Aug. 23, 1997

(86) PCT No.: PCT/GB97/02266

§ 371 Date: Mar. 29, 1999

§ 102(e) Date: Mar. 29, 1999

(87) PCT Pub. No.: WO98/07872

PCT Pub. Date: Feb. 26, 1998

(30) Foreign Application Priority Data

Aug. 23, 1996 (GB) .................................. 9617683

(51) Int. Cl.[7] .................. C12Q 1/34; C12Q 1/00; C12Q 1/32; C12Q 1/54
(52) U.S. Cl. ....................... 435/18; 435/4; 435/975; 435/26; 435/14; 530/300; 536/23.1; 536/23.2; 536/23.72
(58) Field of Search ..................... 435/18, 4, 975, 435/26, 14; 530/300; 536/23.1, 23.2, 23.72

(56) References Cited

U.S. PATENT DOCUMENTS

| | | | |
|---|---|---|---|
| 4,940,658 | 7/1990 | Allen et al. ................. | 435/4 |
| 5,690,929 | 11/1997 | Lishko et al. ............... | 424/94.5 |
| 5,715,835 | 2/1998 | Lishko et al. ............... | 128/898 |
| 5,885,767 | 3/1999 | Rozzell, Jr. ................. | 435/4 |
| 5,985,540 | 11/1999 | Tan et al. .................... | 435/4 |
| 5,998,191 | 12/1999 | Tan et al. .................... | 435/232 |
| 6,066,467 | * 5/2000 | Xu et al. ..................... | 435/23 |
| 6,140,102 | 10/2000 | Tan et al. .................... | 534/232 |

FOREIGN PATENT DOCUMENTS

WO93/15220   8/1993  (WO) .
WO 99/05311  2/1999  (WO) ................ C12Q/1/68

OTHER PUBLICATIONS

Erickson P. et al.; Sequence of cDNA for rat cystathionine γ–lyase and comparison of deduced amino acid sequence with related *Escherichia coli* enzymes, *Biochem. J.*, 269:335–340 (1990).

Lockwood B. e al.; Purification and characterization of methionine γ–lyase from *Trichomonas vaginalis*, *Biochem. J.*, 279:675–682 (1991).

Lu Y. et al.; Cloning and Nucleotide Sequence of Human Liver cDNA Encoding for Cystahionine γ–Lyase, *Biochemical and Biophysical Research Communications*, 189(2): 749–758 (1992).

Thong K. et al.; L–Methionine catabolism in trichomonads, *Molecular and Biochemical Parasitology*, 23:223–231 (1987).

(List continued on next page.)

Primary Examiner—Louise N. Leary
(74) Attorney, Agent, or Firm—Myers Bigel Sibley & Sajovec

(57) ABSTRACT

The present invention relates to an assay for determining homocysteine, cysteine, O-acetyl-L-serine and/or methionine levels in a biological sample using an enzyme that catalyzes the degradation of homocysteine, cysteine, O-acetyl-L-serine and methionine. The enzyme being more particularly homocysteine desulphurase, a polynucleotide fragment encoding protozoan homocysteine desulphurase, a recombinant vector comprising a polynucleotide fragment, transformed cells, the protozoan homocysteine desulphurase polypeptide, and pharmaceutical compositions comprising recombinant homocysteine desulphurase for use in medicine or veterinary medicine.

72 Claims, 5 Drawing Sheets

OTHER PUBLICATIONS

Thong K. et al.; Trichomonad homocysteine desulphurase activity in trichomonads, XP002049553, Paper received Apr. 26, 1985.

Thong K. et al.; Trichomonas Species: Homocysteine Desulphurase and Serine Sulphydrase Activities, *Experimental Parasitology*, 63:143–151 (1987).

* cited by examiner

```
  1 ATTTTTAGACAACATGTCTCACGAGAGAATGACCCCAGCAACAGCATGCATCCATGCTAA
  1                M  S  H  E  R  M  T  P  A  T  A  C  I  H  A  N

61 TCCACAGAAGGATCAGTTTGGAGCAGCCATCCCACCAATCTACCAAACATCAACATTCGT
 21  P  Q  K  D  Q  F  G  A  A  I  P  P  I  Y  Q  T  S  T  F  V

121 TTTCGATAACTGCCAACAGGGTGGAAACAGATTCGCTGGTCAGGAATCCGGCTACATCTA
 41  F  D  N  C  Q  Q  G  G  N  R  F  A  G  Q  E  S  G  Y  I  Y

181 CACACGTCTCGGCAACCCAACAGTTTCAAACCTCGAAGGCAAGATCGCCTTCCTCGAGAA
 61  T  R  L  G  N  P  T  V  S  N  L  E  G  K  I  A  F  L  E  K

241 AACAGAAGCATGCGTTGCCACATCTTCTGGCATGGGTGCCATTGCTGCTACAGTTTTGAC
 81  T  E  A  C  V  A  T  S  S  G  M  G  A  I  A  A  T  V  L  T

301 AATCCTCAAGGCCGGAGATCACTTAATCTCCGATGAGTGCCTTTATGGCTGCACACATGC
101  I  L  K  A  G  D  H  L  I  S  D  E  C  L  Y  G  C  T  H  A

361 TCTCTTTGAGCACGCATTGACAAAGTTCGGCATCCAGGTCGACTTCATCAACACAGCCAT
121  L  F  E  H  A  L  T  K  F  G  I  Q  V  D  F  I  N  T  A  I

421 CCCAGGCGAGGTCAAGAAGCACATGAAGCCAAACACAAAGATTGTCTATTTCGAGACACC
141  P  G  E  V  K  K  H  M  K  P  N  T  K  I  V  Y  F  E  T  P

481 AGCCAACCCAACACTCAAGATCATCGACATGGAGCGCGTCTGCAAGGACGCCCACAGCCA
161  A  N  P  T  L  K  I  I  D  M  E  R  V  C  K  D  A  H  S  Q

541 GGAGGGCGTCTTAGTTATCGCCGATAACACATTCTGCTCACCAATGATCACAAACCCAGT
181  E  G  V  L  V  I  A  D  N  T  F  C  S  P  M  I  T  N  P  V

601 CGACTTTGGCGTCGATGTTGTTGTCCACTCTGCAACAAAGTACATCAACGGCCACACAGA
201  D  F  G  V  D  V  V  V  H  S  A  T  K  Y  I  N  G  H  T  D

661 TGTCGTCGCTGGCCTTATCTGTGGCAAGGCTGACCTCCTTCAACAGATTCGTATGGTTGG
221  V  V  A  G  L  I  C  G  K  A  D  L  L  Q  Q  I  R  M  V  G

721 TATCAAGGATATCACAGGATCTGTTATCAGCCCACACGACGCTTGGCTCATCACACGTGG
241  I  K  D  I  T  G  S  V  I  S  P  H  D  A  W  L  I  T  R  G

781 CCTCTCAACACTCAACATCAGAATGAAGGCTGAGAGCGAGAACGCCATGAAGGTCGCTGA
261  L  S  T  L  N  I  R  M  K  A  E  S  E  N  A  M  K  V  A  E

841 GTACCTCAAATCTCACCCAGCCGTTGAGAAGGTTTACTACCCAGGCTTCGAGGACCACGA
281  Y  L  K  S  H  P  A  V  E  K  V  Y  Y  P  G  F  E  D  H  E

901 GGGCCACGATATCGCTAAGAAGCAGATGAGAATGTACGGTTCAATGATCACATTCATCCT
301  G  H  D  I  A  K  K  Q  M  R  M  Y  G  S  M  I  T  F  I  L

961 CAAGTCCGGCTTCGAAGGCGCTAAGAAGCTCCTCGACAACCTCAAGCTTATCACACTTGC
321  K  S  G  F  E  G  A  K  K  L  L  D  N  L  K  L  I  T  L  A

1021 AGTTTCCCTTGGTGGCTGCGAGTCCCTCATCCAGCACCCAGCTTCAATGACTCACGCTGT
341  V  S  L  G  G  C  E  S  L  I  Q  H  P  A  S  M  T  H  A  V

1081 CGTTCCAAAGGAGGAGCGTGAGGCCGCTGGTATTACAGATGGCATGATCCGCCTTTCTGT
361  V  P  K  E  E  R  E  A  A  G  I  T  D  G  M  I  R  L  S  V

1141 CGGTATTGAAGATGCCGACGAACTCATCGCTGATTTCAAACAGGGCCTTGACGCTCTTTT
381  G  I  E  D  A  D  E  L  I  A  D  F  K  Q  G  L  D  A  L  L

1201 ATAAACTCTACTTAGTTTCTTGACTTTAATTAAAAAAAAAAAAAAAAAA
```

FIG. 1

```
   1 GACTTTATATAAAAGATGAGTGGCCACGCTATCGACCCAACACATACAGACACACTTTCC
   1                   M  S  G  H  A  I  D  P  T  H  T  D  T  L  S
  61 ATCCACGCCAACCCACAGAAGGATCAGTTCGGTGCTATTGTTGCTCCAATCTACCAAACA
  21  I  H  A  N  P  Q  K  D  Q  F  G  A  I  V  A  P  I  Y  Q  T
 121 TCCACCTTCCTCTTCGACAACTGCGACCAGGGTGGTGCTCGTTTCGGTGGCAAGGAAGCC
  41  S  T  F  L  F  D  N  C  D  Q  G  G  A  R  F  G  G  K  E  A
 181 GGTTACATGTACACACGTATCGGTAACCCAACAAACTCCGCACTCGAAGGCAAGATCGCC
  61  G  Y  M  Y  T  R  I  G  N  P  T  N  S  A  L  E  G  K  I  A
 241 AAGCTCGAACACGCTGAGGCATGCGCTGCCACAGCTTCTGGCATGGGTGCTATTGCTGCT
  81  K  L  E  H  A  E  A  C  A  A  T  A  S  G  M  G  A  I  A  A
 301 TCTGTCTGGACATTCCTCAAGGCCGGTGATCACCTTATCTCCGACGATTGCCTTTATGGC
 101  S  V  W  T  F  L  K  A  G  D  H  L  I  S  D  D  C  L  Y  G
 361 TGCACACACGCCCTCTTCGAGCATCAGCTCCGCAAGTTCGGCGTTGAAGTTGATTTCATC
 121  C  T  H  A  L  F  E  H  Q  L  R  K  F  G  V  E  V  D  F  I
 421 GACATGGCTGTCCCAGGAAACATTGAGAAGCACTTGAAGCCAAACACAAGAATCGTCTAC
 141  D  M  A  V  P  G  N  I  E  K  H  L  K  P  N  T  R  I  V  Y
 481 TTCGAAACACCAGCTAACCCAACATTAAAGGTTATCGACATCGAAGACGCCGTCAAGCAG
 161  F  E  T  P  A  N  P  T  L  K  V  I  D  I  E  D  A  V  K  Q
 541 GCCAGAAAGCAGAAGGATATCCTCGTTATCGTTGATAACACCTTCGCTTCACCAATTCTT
 181  A  R  K  Q  K  D  I  L  V  I  V  D  N  T  F  A  S  P  I  L
 601 ACAAACCCACTCGACCTCGGTGTTGATATCGTCGTTCACTCCGCTACTAAGTACATCAAT
 201  T  N  P  L  D  L  G  V  D  I  V  V  H  S  A  T  K  Y  I  N
 661 GGCCACACCGATGTTGTCGCCGGCCTTGTCTGCTCAAGAGCTGACATCATCGCTAAGGTC
 221  G  H  T  D  V  V  A  G  L  V  C  S  R  A  D  I  I  A  K  V
 721 AAGTCCCAGGGTATCAAGGATATCACAGGCGCCATCATTTCCCCACACGACGCTTGGCTC
 241  K  S  Q  G  I  K  D  I  T  G  A  I  I  S  P  H  D  A  W  L
 781 ATCACAAGAGGCACACTTACACTCGATATGCGTGTCAAGCGCGCTGCCGAGAACGCTCAG
 261  I  T  R  G  T  L  T  L  D  M  R  V  K  R  A  A  E  N  A  Q
 841 AAGGTCGCTGAATTCCTCCATGAGCACAAGGCCGTCAAGAAGGTCTACTACCCAGGCCTT
 281  K  V  A  E  F  L  H  E  H  K  A  V  K  K  V  Y  Y  P  G  L
 901 CCAGACCATCCAGGCCACGAAATCGCCAAGAAGCAGATGAAGATGTTCGGCTCTATGATC
 301  P  D  H  P  G  H  E  I  A  K  K  Q  M  K  M  F  G  S  M  I
 961 GCATTCGATGTCGACGGATTAGAGAAGGCCAAGAAAGTCCTTGACAACTGCCACGTTGTT
 321  A  F  D  V  D  G  L  E  K  A  K  K  V  L  D  N  C  H  V  V
1021 TCTCTCGCCGTTTCCCTCGGTGGTCCAGAATCCCTCATCCAGCACCCAGCTTCAATGACA
 341  S  L  A  V  S  L  G  G  P  E  S  L  I  Q  H  P  A  S  M  T
1081 CACGCTGGTGTTCCAAAGGAGGAACGCGAGGCTGCTGGCCTAACAGATAACCTCATCCGC
 361  H  A  G  V  P  K  E  E  R  E  A  A  G  L  T  D  N  L  I  R
1141 CTCTCTGTTGGCTGTGAGAACGTTCAGGATATCATCGACGACCTCAAGCAGGCTCTCGAC
 381  L  S  V  G  C  E  N  V  Q  D  I  I  D  D  L  K  Q  A  L  D
1201 TTAGTCCTCTAAATTTAACTTTCGAATTTCAGTAATAAAATCCTAGATATCTTCCCCCCC
 401  L  V  L  -
     CAAAAAAAAAAAAAAAAAAAAAAAAAAAAAAAAAAAAAAAAAAAA
```

FIG. 2

```
           1                                                     50
CYHUMAN    MQEKDASSQG FLPHFQHFAT QAIHVGQDPE QWTSRAVVPP ISLSTTF...
  CYRAT                                         CCGAA  HLLATTF...
CYYEAST             M TLQESDKFAT KAIHAGEHVD VHGS..VIEP ISLSTTF...

51                                                    100
CYHUMAN    ..KQGAP..G QHSG.FEYSR SGNPTRNCLE KAVAALDGAK YCLAFASGLA
  CYRAT    ..KQDSP..G QSSG.FVYSR SGNPTRNCLE KAVAALDGAK HCLTFARGLA
CYYEAST    ..KQSSP..A NPIGTYEYSR SQNPNRENLE RAVAALENAQ YGLAFSSGSA 101                                                   150
CYHUMAN    A.TVTITHLL KAGDQIICMD DVYGGTNRYF RQVASEFGLK ISFVDCSKIK
  CYRAT    A.TTTITHLL KAGDEVICMD EVYGGTNRYF RRVASEFGLK ISFVDCSKTK
CYYEAST    T.TATILQSL PQGSHAVSIG DVYGGTHRYF TKVANAHGVE TSFTN.DLLN 151                                                   200
CYHUMAN    LLEAAITPET KI|VWIETPTN| PTQKVIDIEG CAHIVHKHG. ..DIILVVDN
  CYRAT    LLEAAITPQT KI|VWIETPTN| PTLKLADIKA CAQIVHKHK. ..DIILVVDN
CYYEAST    DLPQLIKENT KI|VWIETPTN| PTLKVTDIQK VADLIKKHAA GQDVILVVDN 201                                                   250
CYHUMAN    TFMSPYFQRP LALGADISMY S|ATKYMNGH|S DVVMGLVSVN CESLHN.RLR
  CYRAT    TFMSAYFQRP LALGADICMC S|ATKYMNGH|S DVVMGLVSVN SDDLNE.RLR
CYYEAST    TFLSPYISNP LNFGADIVVH S|ATKYINGH|S DVVLGVLATN NKPLYE.RLQ 251                                                   300
CYHUMAN    FLQNSLGAVP SPIDCYLCNR GLKTLHVRME KHFKNGMAVA QFLESN.PWV
  CYRAT    FLQNSLGAVP SPFDCYLCCR GLKHCRSGWR NTFQDGMAVA RFLESN.PRV
CYYEAST    FLQNAIGAIP SPFDAWLTHR GLKTLHLRVR QAALSANKIA EFLAADKENV 301                                                   350
CYHUMAN    EKVIYPGLPS HPQHELVKRQ CTGC..TGMV TFYIKGTLQH AEIFLKNLKL
  CYRAT    EKVIYPGLPS HPQHELAKRQ ARAC..PGMV SFYIKGTLQH AQVFLKNIKL
CYYEAST    VAVNYPGLKT HPNYDVVLKQ HRDALGGGMI SFRIKGGAEA ASKFASSTRL 351                                                   400
CYHUMAN    FTLAESLGGF ESLAELPAIM THASVLKNDR DVLGISDTLI RLSVGLEDEE
  CYRAT    FALAESLGGY ESLAELPAIM THASVPEKDR ATLGISDTLI RLSVGLEDEK
CYYEAST    FTLAESLGGI ESLLEVPAVM THGGIPKEAR EASGVFDDLV RISVGIEDTD 401              422
CYHUMAN    DLLEDLDQAL KAAHPPSGIH S*
  CYRAT    DLLEDLGQAL KAAHP*.... ..
CYYEAST    DLLEDIKQAL KQATN*.... ..
```

CYST 5'

```
5'    GCAAGCTTGTITGGATTGAGACICCIACGAA    3'
      HindIII        C           A
                     A           T
                                 C
```

CYST 3'

```
5'    GCCTCGAGCCGTTIATGTACTTIGTAGC    3'
      XhoI          A T       G
                              C
                              T
```

FIG. 5

5' NcoI PRIMER

```
5'    CGCCATGGCTCACGAGAGAATGAC    3'
        NcoI
```

3' BglII PRIMER

```
5'    GCAGATCTTAAAAGAGCGTCAAGGCCC    3'
        BglII
```

FIG. 6

THE NUCLEOTIDE SEQUENCE OF MUTATED *mgl1* AND THE MGL1 (C113G) AMINO ACID SEQUENCE ARE IDENTICAL TO THAT OF *mgl1*/MGL1 WITH THE FOLLOWING CHANGE (THE CHANGE BEING SHOWN UNDERLINED):

```
332   GATGAGGGCCTTTAT   346
111    D   E   G   L   Y    115
```

FIG. 7

THE NUCLEOTIDE SEQUENCE OF MUTATED *mgl2* AND THE MGL2 (C116G) AMINO ACID SEQUENCE ARE IDENTICAL TO THAT OF *mgl2*/MGL2 WITH THE FOLLOWING CHANGE (THE CHANGE BEING SHOWN UNDERLINED):

```
343   GACGATGGCCTTTAT   357
       D   D   G   L   Y    119
```

US 6,306,618 B1

HOMOCYSTEINE DESULPHURASE FROM THE PROTOZOAN TRICHOMONAS VAGINALIS

FIELD OF THE INVENTION

The present invention relates to an assay for determining homocysteine, cysteine, O-acetyl-L-serine and/or methionine levels in a biological sample using a enzyme which catalyses the degradation of homocysteine, cysteine, O-acetyl-L-serine and/or methionine, the enzyme being particularly homocysteine desulphurase; a polynucleotide fragment encoding protozoan homocysteine desulphurase, a recombinant vector comprising such a polynucleotide fragment, a host cell containing said polynucleotide fragment or said recombinant vector, the protozoan homocysteine desulphurase polypeptide, and pharmaceutical compositions comprising recombinant homocysteine desulphurase for use in medicine or veterinary medicine.

BACKGROUND OF THE INVENTION

An elevated level of homocysteine in the blood appears to be an important indicator for many human disease states. Homocysteine is predictive of vascular disease and stroke, Ueland, P. M. (1992) and Kluijtmans L. A. J. et al (1996); is correlated with forms of diabetes and alcoholism, Cravo, M. L. et al (1996); is used to monitor liver and kidney damage, Bostom, A. G. et al (1996) and neural tube defects, Steegers-Theunissen, R. P. N. (1992) and is associated with certain inborn errors of metabolism, Mudd, S. H., (1989).

Homocysteine levels in blood are conventionally determined using high performance liquid chromatography (HPLC) methods, see for example at Poele-Pothoff M. T. B. et al, (1995). However, HPLC methods employ expensive and elaborate machinery, are generally sophisticated and are considered impractical for many routine analyses.

Patent publication WO93/15220 (Cockbain) describes a method for assaying homocysteine in blood using a homocysteine converting enzyme, S-adenosyl homocysteine hydrolase (SAH-hydrolase). SAH-hydrolase catalyses the conversion of homocysteine with a co-substrate, adenosine, to S-adenosyl-homocysteine. It is then possible, by determining the amount of adenosine consumed, to make a correlation with the amount of homocysteine consumed. The amount of homocysteine in a sample is then determined from differences in adenosine concentration. However, such an assay requires the use of two initial substrates (homocysteine and adenosine) and two enzymes, making it relatively complex. It also involves determining a decrease in the concentration of adenosine, which may not be satisfactory.

U.S. Pat. No. 4,940,658 (Allen et al) describes a method for determining sulphydryl amino acids, including homocysteine levels, in samples of body tissues, method of detecting cobalamin and folic acid deficiency using an assay for total homocysteine levels, and methods for distinguishing cobalamin from folic acid deficiency using an assay for total homocysteine levels in conjunction with an assay for methylmalonic acid. The assays comprise combining a sample with a reference standard comprising a known amount of a sulphydryl amino acid to be assayed, labelled with a suitable marker and measuring the relative amounts of labelled and unlabelled sulphydryl amino acid present for each species with a mass spectrometer. As the amount of labelled species is known, it is therefore possible from calculating the ratio of labelled to unlabelled species to determine the amount of sulphydryl amino acid present in the sample.

U.S. Pat. No. 5,438,017 describes a gas chromatography/mass spectrometry method for analysis of sulphydryl amino acids in a sample of body fluid. The assay relies on the use of a labelled reference sulphydryl amino acid, similar to that described in U.S. Pat. No. 4,940,658, but has additional treatment and/or purification steps prior to analysing the sample by gas chromatography/mass spectrometry.

It will be appreciated that similar to HPLC methods, the assays described above which employ gas chromatography/mass spectrometry are generally sophisticated, use expensive and elaborate machinery and are considered impractical for many routine analyses.

SUMMARY

It is an object to the present invention to provide an assay which obviates and/or mitigates at least some of the above disadvantages.

It is a further object of the present invention to provide a recombinant enzyme capable of catalysing the degradation of homocysteine including use in said assay.

BRIEF DESCRIPTION OF THE DRAWINGS

FIG. 1 provides the nucleotide sequence of the Mgl1 cDNA (SEQ ID NO:1) and MGL1 amino acid sequence (SEQ ID NO:2).

FIG. 2 provides the nucleotide sequence of the Mgl2 cDNA (SEQ ID NO:3) and MGL2 amino acid sequence (SEQ ID NO:4).

FIG. 3 compares amino acid sequences of cystathionine γ-lyase from human (cyhuman), rat (cyrat) and yeast (cyyeast). The regions of homology used to design primers are boxed.

FIG. 4 provides the sequences of degenerate oligonucleotide primers designed based on the homologous regions of cystathionine γ-lyase shown in FIG. 3.

FIG. 5 provides the sequences of two primers designed to the 5' and 3' ends of the mgl1 cDNA, including the restriction endonuclease sites NcoI and BglII.

FIG. 6 provides the nucleotide sequence (SEQ ID NO:5) and amino acid sequence (SEQ ID NO:6) of the mutated mgl1.

FIG. 7 provides the nucleotide sequence (SEQ ID NO:7) and amino acid sequence (SEQ ID NO:8) of the mutated mgl2.

DETAILED DESCRIPTION

The present invention provides a polynucleotide fragment such as a DNA fragment, encoding protozoan homocysteine desulphurase. The invention further provides a recombinant protozoan homocysteine desulphurase polypeptide.

"Homocysteine desulphurase" as used herein refers to an enzyme that is capable of catalysing the degradation of homocysteine to release α-ketobutyrate, hydrogen sulphide, and ammonia.

$$HS-CH_2-CH_2-CH(NH_2)COOH \rightarrow CH_3-CH_2-C(O)COOH + H_2S + NH_3$$

Such an enzyme may also possess an affinity for other substrates such as methionine, cysteine and O-acetyl-L-serine. For example if methionine is used as a substrate, the end products of catabolism by the enzyme are α-ketobutyrate, ammonia and methanethiol.

It should be appreciated that there may be several forms (eg. from different organism) or isoforms, of "homocysteine desulphurase" and all such forms/isoforms and uses thereof are encompassed herein.

"Polynucleotide fragment" as used herein refers to a chain of nucleotides such as deoxyribose nucleic acid (DNA) sequences and transcription products thereof, such as RNA, capable of giving rise to a homocysteine desulphurase or a physiologically functional derivative thereof. A physiologically functional derivative is one in which the enzyme functionality identifies an enzyme as a homocysteine desulphurase as hereinbefore defined. Thus, this term includes double and single stranded DNA, and RNA sequences derived therefrom. The term excludes the whole naturally occurring genome comprising the polynucleotide fragment, as found for example in the protozoon *Trichomonas vaginalis*.

Generally, the polynucleotide will be in substantially isolated form. That is, substantially free of biological material with which the whole genome is normally associated in vivo.

In general, the term "polypeptide" refers to a chain or sequence of amino acids displaying a biological activity substantially similar to the biological activity of homocysteine desulphurase and does not refer to a specific length of the product as such. The polypeptide if required, can be modified in vivo and/or in vitro, for example by glycosylation, amidation, carboxylation, phosphorylation and/or post translational cleavage, thus inter alia, peptides, oligo-peptides, proteins and fusion proteins are encompassed thereby. Naturally the skilled addressee will appreciate that modified polypeptide should retain physiological function i.e. be capable of homocysteine desulphurase activity.

The DNA fragment encoding homocysteine desulphurase can be obtained by utilising a partial homocysteine desulphurase cDNA. The cDNA may be obtained by reverse transcription of messenger RNA followed by amplification typically using polymerase chain reaction (PCR) techniques known in the art, for example, using primers designed against conserved regions of related enzymes such as cystathionine γ-lyase coding sequences e.g. human, rat and/or yeast cystathionine γ-lyase. The amplified fragment containing a portion of the homocysteine desulphurase gene can then be used to clone the entire homocysteine desulphurase gene from a cDNA library comprising such a gene. The cDNA library may be from a protozoan, for example a *Trichomonas vaginalis* cDNA library. Polynucleotide fragments containing homocysteine desulphurase genes obtained in such a way are depicted in FIGS. 1 and 2 (SEQ ID NO: 1 and SEQ ID NO:3).

The DNA fragment of FIG. 1 (SEQ ID NO:1) encodes a gene ctlα (subsequently renamed as mgl1) comprising an open reading frame (ORF) of 396 amino acids (SEQ ID NO:2) hereinafter referred to as CTLα (subsequently renamed as MGL1). The DNA fragment of FIG. 2 (SEQ ID NO:3) encodes a gene ctlβ (subsequently renamed as mgl2) comprising an ORF of 398 amino acids (SEQ ID NO:4) hereinafter referred to as CTLβ (subsequently renamed as MGL2). A comparison of the percentage identity (at the amino acid level) of MGL1 and MGL2 as depicted in FIGS. 1 and 2 with methionine γ-lyase from *Pseudomonas putida* and cystathionine γ-lyase from yeast and human (EMBL database accession numbers, D30039, P31373 and S52784, respectively) is shown in table 1. Sequence comparison analysis was performed using gap and pileup programs using the GCG Wisconsin package (Devereux, H., Hacberli, P. Smithies, O. (1984) Nucleic Acids Research 12, 387–395).

TABLE 1

| | MGL 1 | MGL 2 | P.putida methionine γ-lyase I | yeast cystathionine γ-lyase | human cystathionine γ-lyase |
|---|---|---|---|---|---|
| MGL1 | — | 69% | 44% | 44% | 42% |
| MGL2 | | — | 45% | 43% | 43% |
| P.putida methionine γ-lyase | | | — | 40% | 45% |
| yeast cystathionine γ-lyase | | | | — | 52% |

Table 1 shows that the putative homocysteine desulphurase enzymes as depicted in FIGS. 1 and 2 (SEQ ID NO:2 and SEQ ID NO:4) are only 42–45% identical, at the amino acid level, with previously sequenced methionine γ-lyase and cystathionine γ-lyases. Thus, although MGL1 and MGL2 may have been cloned using primers designed against conserved regions of cystathionine γ-lyase, they are not substantially similar over the length of the polypeptides.

The present invention also includes polynucleotide fragments having at least 80%, particularly at least 90% and especially at least 95% similarity with the fragment exemplified in FIGS. 1 and 2 (SEQ ID NO:1 and SEQ ID NO:3). The present invention also includes polypeptide sequences having at least 80%, particularly at least 90% and especially at least 95% similarity with the polypeptide exemplified in FIGS. 1 and 2 (SEQ ID NO:4). "Similarity" refers to both identical and conservative replacement of nucleotides or amino acids, provided that the enzymic functionality of the homocysteine desulphurase is substantially unimpaired.

The skilled addressee will appreciate that it is possible to genetically manipulate the gene or derivatives thereof, for example, to clone the gene by recombinant DNA techniques generally known in the art and to express the polypeptides encoded thereby in vitro or in vivo. Polynucleotide fragments having the nucleotide sequences depicted in FIGS. 1 and 2, or derivatives thereof, are preferably used for the expression of homocysteine desulphurase.

It will be understood that for the particular homocysteine desulphurase polypeptides embraced herein, variations (natural or otherwise) can exist. These variations may be demonstrated by (an) amino acid difference(s) in the overall sequence or by deletions, substitutions, insertions, inversions or additions of (an) amino acid(s) in said sequence. All such derivatives are included within the scope of this invention provided that the derivatives are physiologically functional (ie display homocysteine desulphurase activity as defined herein). For example, for the purpose of the present invention conservation replacements may be made between amino acids, within the following groups:

(I) alanine, serine and threonine;

(II) glutamic acid and aspartic acid;

(III) arginine and lysine;

(IV) asparagine and glutamine;

(V) isoleucine, leucine and valine;

(VI) phenylalanine, tyrosine and tryptophan.

Moreover, specific replacements of amino acids identified to be within putative functional domains of homocysteine desulphurase may be carried out. For example amino acids identified within a putative substrate binding domain may be replaced with conservative or non-conservative amino acids in order to observe any changes in the enzyme's kinetics such replacements make. Such changes may for example result in an increase in specific activity for homocysteine, or reduce specific activity while decreasing the Km for homocysteine, or increase specific activity for other substrates such as cysteine and O-acetyl-L-serine.

The present inventors have shown that a cysteine residue C113 in MGL1 and C116 in MGL2 plays some part in the homocysteine desulphurase catalytic activity. They have shown that replacement of cysteine 113/116 with glycine (SEQ ID NO: 6 and SEQ ID NO: 8) still results in a catalytically active homocysteine desulphurase. Although this mutation generally results in an enzyme with reduce specific activity towards all substrates, mutation of cysteine 116 in MGL2 to glycine results in an enzyme with increased specific activity towards cysteine and O-acetyl-L-serine. Moreover mutation of cysteine 116 in MGL2 to glycine (SEQ ID NO: 8) results in an enzyme with a lower Km for homocysteine.

In addition the MGL1 and MGL2 sequences have been observed to have a 7 amino acid insertion relative to the cystathionine γ-lyases towards the N-terminus (residues 49–55 in MGL1). Such a region may be suitable for mutation studies.

Mutation studies may allow different homocysteine desulphurases to be produced with differing catalytic activities, which may be suitable for a number of different uses.

Moreover, recombinant DNA technology may be used to prepare nucleic acid sequences encoding these derivatives as outlined above.

As is well known in the art, the degeneracy of the genetic code permits substitution of bases in a codon resulting in a different codon capable of coding for the same amino acid, e.g. the codon for the amino acid glutamic acid is both GAT and GAA. Consequently, it is clear that for the expression of a polypeptide with the amino acid sequence shown in FIGS. 1 or 2, or a fragment thereof, use can be made of a derivative nucleic acid sequence with such an alternative codon composition different for the nucleic acid sequence shown in FIG. 1 or 2.

Furthermore, fragments derived from the homocysteine desulphurase polypeptides or from the amino acid sequences depicted in FIGS. 1 and 2 which display homocysteine desulphurase activity, or fragments derived from the nucleotide sequence encoding said homocysteine desulphurase polypeptide or derived from the nucleotide sequence depicted in FIGS. 1 and 2 encoding fragments of said homocysteine desulphurase polypeptides are also included in the present invention.

Naturally the skilled addressee will appreciate that such modifications mentioned hereinabove resulting in enzymically active derivatives of said homocysteine desulphurase polypeptide or gene are encompassed by the present invention. Said homocysteine desulphurase polynucleotide fragments of the present invention are preferably linked to regulatory control sequences. Such control sequences may comprise promoters, operators, inducers, ribosome binding sites, terminators etc. Suitable control sequences for a given host may be selected by those of ordinary skill in the art. Additionally so-called "tagging sequences" such as additional amino acids may be added to the N or C terminus of the polypeptide, to give a so-called fusion protein upon expression of the polypeptide.

A polynucleotide fragment according to the present invention can be ligated to any one or more of a variety of expression controlling DNA sequences, resulting in a so-called recombinant DNA molecule. Thus, the present invention also includes an expression vector comprising an expressible nucleic acid molecule. Such recombinant nucleic acid molecules can then be used for the transformation of a suitable host. The expression vectors are preferably hybrid DNA molecules derived from, for example, plasmids, or from nucleic acid sequences derived from bacteriophage or viruses and are termed "vector molecules".

Specific vectors which can be used to clone nucleic acid sequences according to the present invention are known in the art (e.g. Rodriguez, R. L. and D. T. Denhardt, Edit., Vectors: A Survey of Molecular Cloning Vectors and Their Uses, Butterworths, 1988).

Two specific bacterial expression vectors pQE60 and pQE30 (Qiagen Hilden, Germany) have been used for homocysteine desulphurase expression. The pQE series of expression vectors (e.g. pQE60 and pQE30) encode a 6 histidine tag (6xhis-tag) which enables the purification of fusion protein using metal-chelate affinity chromatography and Fast Protein Liquid Chromatography (FPLC).

The methods used in the construction of a recombinant nucleic acid molecule according to the present invention are known to the skilled addressee and are inter alia set forth in Sambrook, et al. (Molecular Cloning: A Laboratory Manual, Cold Spring Harbour Laboratory, 1989).

The present invention also relates to a transformed cell containing the nucleic acid molecule in expressible form. "Transformation" as used herein, refers to the introduction of a heterologous nucleic acid sequence into a host cell, irrespective of the method used, for example direct uptake, transfection or transduction. The heterologous polynucleotide fragment may be maintained through autonomous replication or alternatively, may be integrated into the host genome. The recombinant nucleic acid molecule preferably is provided with an appropriate control sequence compatible with a designated host which can regulate the expression of an inserted polynucleotide fragment e.g. T7 promoter, taq promoter, lac promoter and trp promoter.

Suitable hosts used for the expression of recombinant nucleic acid molecules can be prokaryotic or eukaryotic in origin. The most widely used hosts for expression of recombinant nucleic acid molecules may be selected from bacteria, yeasts, insect cells and mammalian cells. The cloning and expression of recombinant homocysteine desulphurase also facilitates in producing reagents for the production of, for example, probes for in situ expression studies, production of anti-homocysteine desulphurase antibodies (particularly monoclonal antibodies) and evaluation of in vitro and in vivo biological activity of recombinant homocysteine desulphurase.

The present invention further provides recombinant homocysteine desulphurase for the manufacture of reagents for use as prophylactic and/or therapeutic agents. In particular, the present invention provides pharmaceutical compositions comprising the recombinant homocysteine desulphurase together with a pharmaceutically acceptable carrier therefore. Disease states such as cancer may benefit from homocysteine desulphurase therapy and/or prophylactic treatment in a manner similar to that described by Hori, H. et al. (1996) for methionine γ-lyase. Typically homocysteine desulphurase may be used in the development of new antitrichomonal drugs, compounds that may well also have useful activity against other pathogens that contain homocysteine desulphurase and/or methionine γ-lyase. These include both using the recombinant homocysteine to screen for inhibitors in for example combinatorial libraries and also analysis of the enzyme's structure in order to provide the design of specific inhibitors or pro-drugs.

The present invention provides means with which homocysteine levels may be assayed.

Thus, in a further aspect the present invention provides a method assaying homocysteine in a sample, comprising the steps of:
a) contacting the sample with an enzyme capable of degrading homocysteine, and
b) determining any reaction product(s) formed by enzymic degradation of homocysteine by said enzyme.

Preferably chromatographic separation of homocysteine and/or said reaction product(s) is not carried out.

Preferably the enzyme is homocysteine desulphurase, more preferably is recombinant protozoan homocysteine desulphurase.

Preferably the homocysteine desulphurase is the homocysteine desulphurase according to FIG. 1, 2 or 6 7 (SEQ ID NO:2, SEQ ID NO:4, SEQ ID NO:6, and SEQ ID NO:8).

Recombinant protozoan homocysteine desulphurase may also be used to assay other substrates in a sample, including methionine, cysteine and O-acetyl-L-serine.

Generally the biological sample may be a sample of blood, plasma, faeces, saliva, vaginal fluids or urine. Homocysteine may be bound by disulphide linkage to circulating proteins, such as albumin, and homocysteine may also be present in the form of other disulphide derivatives (typically homocysteine-cysteine conjugates). To obtain an estimate of total homocysteine present in the sample it may therefore be desirable to treat the sample with a reducing agent to cleave any disulphide bonds and liberate free homocysteine. Disulphide reduction is reviewed by Jocelyn in Methods of Enzymology 143: 243–256 (1987) where a wide range of suitable reducing agents are listed. Such suitable reducing agents are incorporated in the teaching of the present invention.

Conveniently, the end products of the reaction described hereinbefore α-ketobutyrate, hydrogen sulphide and ammonia, may be determined and a variety of suitable methods will be known to the skilled addressee for example, colorimetric, spectrophotometric, electrochemical, fluorimetric or luminescent methods. Preferably the method is sensitive enough to detect concentration of <5 μmol/l homocysteine in a sample.

α-ketobutyrate generated by the degradation of homocysteine may be detected following the method of Soda (Soda, K. (1968) Anal. Biochem. 25: 228–235) using 3-methyl-2-benzothiazolone hydrazone hydrochloride (MBTH).

An additional method of determining α-ketobutyrate is described by Li, R.+Kenyon, G. L. (1995) A spectrophotometric determination of α-dicarboxyl compounds and its application to the enzymatic formation of α-ketobutyrate. *Analytical Biochemistry* 230 37–40.

A particularly preferred method of detecting α-ketobutyrate is by adding NADH and lactate dehydrogenase so as to convert the α-ketobutyrate to α-hydroxybutyrate with the generation of NAD$^+$. The level of NAD$^+$ can then be measured by a number of methods involving conversion to NADH including spectrophotometrically by absorbance at 340 nm; fluorescently by excitation at 365 nm and emission at 460 nm (Palmer T. (1991) Understanding Enzymes 3rd Edition, Ellis Horwood, London); colorimetrically using tetrazolium salts (Altman, P. F. (1974) Histochemistry 38 p155–171); electrochemically (Morroux J. Elring P J (1979) Anal Chem 51, 346; Blaedel W J, Jenkins R A (1975) Anal Chem 47, 1335; Juegfeldt H et al (1981) Anal Chem 53, 1979; Wang J, Lin M S (1987) Electroanal Chem 221, 257); and luminescently (Whitehead T P et al (1979) Clin Chem 25, 1531) As an alternative, pyruvate dehydrogenase may be used in place of lactate dehydrogenase to generate NAD$^+$ and NAD$^+$ detected as described above.

Hydrogen sulphide generated by homocysteine degradation may be determined, for example, by reacting with lead acetate to produce lead sulphide according to the following (stoichiometric) equation.

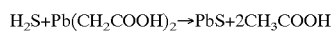

$H_2S + Pb(CH_2COOH)_2 \rightarrow PbS + 2CH_3COOH$

Lead sulphide produced may then be measured spectrophotometrically at a suitable wavelength, such as A360 nm. Thong K. W.+Coombs, G. H. (1985) Homocysteine desulphurase activity in trichomonads. IRCS Medical Science 13 493–494).

Alternatively hydrogen sulphide, may be measured using the methylene blue method as described by Clime, J. D. Limnol, Oceanogr. (1969) 14: 454–458. Briefly, hydrogen sulphide is reacted with 0.17 mM, N,N-dimethyl-p-phenylene diamine sulphate in acid and ferric chloride in acid to produce methylene blue which can be detected spectrophotometrically at 650–670 nm.

Ammonia generated by the degradation of homocysteine may be reacted with phenol in the presence of hypochlorite to produce indophenol as described by Horn, D. B.+Squire, C. R. (1967). An improved method for the detection of ammonia in blood plasma *Clin. Chem. Acta* 17 99–105. Indophenol so produced may then be detected spectrophotometrically at a suitable wavelength, for example, 570 nm.

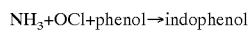

$NH_3 + OCl + phenol \rightarrow indophenol$

Further methods for detecting ammonia include: enzymatically, using α-ketoglutarate and NAD(P)$^+$ with glutamate dehydrogenase as described by Mondzac A et al (1965) J. Lab. Clin. Med. 66 526; electrochemically using an ammonia electrode as described by Guilbault et al (1985) Anal. Chem. 57 2110; using 2-oxoglutarate and NADH to generate glutamate, water and NAD$^+$ and then measuring NAD$^+$ as described above; and adding silver nitrate to ammonia to generate a black precipitate.

The recombinant homocysteine desulphurase according to the present invention displays activity towards a number of substrates, in addition to homocysteine, including methionine, cysteine and O-acetyl-L-serine. It is appreciated therefore that homocysteine desulphurase may be used to assay for methionine, cysteine and/or O-acetyl-L-serine in a manner similar to that described above.

Furthermore as the recombinant homocysteine desulphurase of the present invention displays activity to a wide range of substrates, the enzyme may be used in the synthesis of unusual amino acids and related molecules.

Additionally homocysteine desulphurase may be used to remove homocysteine, methionine and/or cysteine from solutions, for instance from biological media.

Homocysteine desulphurase may also be used to assay for enzymes that catalyse reactions involving homocysteine as either substrate or product (for instance S-adenosylhomocysteine hydrolase). The homocysteine could be assayed in the ways applied to its detection in biological samples. Similarly homocysteine desulphurase may be used to assay enzymes that catalyse reactions involving methionine or cysteine or related compounds as substrates or products. These metabolites could be assayed via their conversion to α-keto acids by homocysteine desulphurase and the measurement of the α-keto acids as described previously.

The assay may also be used to estimate an analyte which is first broken down into homocysteine and then the concentration of the analyte is determined by measuring the concentration of homocysteine. Examples of such analytes include homocysteine (where homocystine is converted to homocysteine using DTT) or methionine (which may be enzymatically converted to homocysteine). In both cases the concentration of analyte could thus be determined by measurement of homocysteine.

In a yet further aspect there is provided a kit for diagnostic in vitro determination of a homocysteine level in a sample, wherein the kit comprises:

a) an enzyme capable of degrading homocysteine, and b) means for enabling determination of reaction products produced by degradation of homocysteine by the enzyme.

Preferably the enzyme is homocysteine desulphurase, more preferably recombinant protozoan homocysteine desulphurase.

Typically the kit may be in the form of a cuvette based test kit for manual and automated use, microtiter plate test kit or test strip based assay kit.

A particularly preferred kit for diagnostic in vitro determination of a homocysteine level in a sample, comprises:

a) recombinant protozoan homocysteine desulphurase, and b) lactate dehydrogenase and NADH for converting α-ketobutyrate, generated by the degradation of homocysteine by said homocysteine desulphurase, into α-hydroxybutyrate with the concomitant release of $NAD^+$, said release of $NAD^+$ being determined by suitable means.

The present invention will now be further described by way of the following non-limiting examples.

EXAMPLE 1

Design of Primers Used to Clone *Trichomonas vaginalis* Homocysteine Desulphurase FIG. 3 shows the multiple protein sequence alignment for cystathionine γ-lyase from human, rat and yeast (SEQ ID NO:11, SEQ ID NO:12 and SEQ ID NO:13, respectively) (Lu et al, 1992, Erickson et al, 1990 and Ono et al, 1992 respectively). Highlighted are the regions of homology chosen for the design of degenerate oligonucleotides to use as primers in polymerase chain reactors (PCRs). The first region of homology chosen for the design of the 5' oligonulceotide primer was a region in which the sequence between the different cystathionine γ-lyase molecules was highly homologous (V163-N170). The second region chosen for the design of the 3' primer was the pyridoxal 5'-phosphate (PLP) binding domain (A222-G228). The sequences of the degenerate oligonucleotides which were designed based upon these homologous regions is shown in FIG. 4 (SEQ ID NOS: 14<21). In order to facilitate cloning, restriction sites for the enzymes in Hind III and Xho I were tagged onto the end of the two degenerate oligonucleotides respectively. The two oligonucleotides were designated Cyst 5' and Cyst 3'. Cyst 5' is 31 nucleotides in length and contains 3 inosines (I) and Cyst 3' is 28 nucleotides in length and contains 2 inosine residues. The inosines were introduced at a number of positions which would have contained four fold degeneracy, in order to reduce the resulting pool of oligonucleotides synthesised. The oligonucleotides were synthesised using an Applied Biosystems DNA synthesiser according to standard protocols.

EXAMPLE 2

PCRs Using the Degenerate Oligonucleotides
RNA Isolation

A clonal cell line (G3) of *T. vaginalis* was grown in modified Diamond's medium as previously described, Lockwood et al. (1984). Cells were harvested (2300 g for 15 min at 4° C.) in late-phase of growth ($1–2 \times 10^6$/ml) and washed twice in 0.25M sucrose. DNA was isolated using a Nucleon II kit (Scotlab, Coatbridge, Scotland).

Total RNA was isolated from *T. vaginalis* in a single step using the commercially available TRIZOL (RTM) reagent (available from Gibco, Paisley, Scotland), which is a monophasic solution of phenol and guanidine isothiocyanate, according to the manufacturer's instructions.

$Poly[A]^+$ RNA was isolated from total RNA for use as a template for cDNA synthesis. $Poly[A]^+$ RNA was isolated using $Poly[A]^+$ Quik columns, (available from Stragene, La Jolla, Calif., USA) according to the manufacturer's instructions.

One microgram of $poly[A]^+$ RNA from *T. vaginalis* along with reverse transcriptase was used to synthesise first strand *T. vaginalis* cDNA according to procedures as described in Sambrook et al (1989). The cDNA was then used as a template in PCRs with the degenerate oligonucleotides.

Conditions of the PCRs were as follows: initial denaturation at 94° C. for 4 minutes followed by 30 amplification cycles consisting of; 94° C. for 1 minute, 42° C. for 1 minute and 72° C. for 1 minute, followed by a final extension cycle at 72° C. for 5 minutes. Portions of the reactions were electrophoresed on an agarose gel (1.5%) together with appropriate control reactions. Two PCR products were observed upon staining the agarose gel, one of approximately 200 base pairs (bp) in size (lower band fragment) and a second of approximately 250 bp in size (upper band fragment).

Additional identical PCRs were performed in order to obtain enough material for cloning.

EXAMPLE 3

Cloning of Amplified PCR Products

Material from several PCR reactions (about 1 μg of DNA) were combined together and the PCR amplified DNA was phenol/chloroform extracted, ethanol precipitated and resuspended in $H_2O$, to remove contaminating nucleotides and Taq polymerase. The amplified DNA was then restricted to completion with HindIII and XhoI restriction enzymes (the restriction sites for these had been engineered onto the ends of the amplified DNA by their inclusion at the termini of the Cyst 5' and Cyst 3' degenerate oligonucleotides respectively) to generate "sticky ends" which would facilitate directional cloning. The DNA was purified further by electrophoresis on a 2% TAE agarose gel followed by staining with ethidium bromide and visualisation under long wave UV light. The amplified bands of interest (upper and lower band products) were excised from the gel using a clean scalpel blade, and the DNA was eluted from the agarose gel slices under commercially available Spinxcolumns (available from Costar, Cambridge, Mass., USA) according to the manufacturer's instructions. The restricted, purified DNA (individual upper band and lower band products and a combination of the two) arising from the PCRs with the degenerate primers, was then combined with pBluescript (available from Stratagene, La Jolla, Calif., USA) which had also been previously restricted with Hind III and Xho I, and purified through a 2% TAE agarose gel and eluted using a spin X column, as before. The pBluescript and amplified PCR fragments of approximately 200 and 250 bp were ligated in quantities of 200 ng insert plus 200 ng vector using the Amersham ligation kit (available from Amersham, Little Chalfort, Bucks, UK), according to the manufacturer's instructions.

The ligation reactions were then used to transform ultra-competent XL1 Blue *Escherichia coli* cells (available from Stratagene, La Jolla, Calif., USA). Approximately 30 to 40 ng of ligated DNA was used to transform the competent bacterial cells. Transformation mixes were plated onto LB amp, X-gal, IPTG containing plates, and incubated overnight at 37° C. Plasmid DNA was isolated from white bacterial transformants using the Wizard plasmid mini-prep procedure of Promega (Promega, Madison, Wis., USA) and subjected to selective restriction analysis to ascertain whether cloning of the amplified DNA into pBluescript had been successful.

Transformants containing the cloned PCR products were subjected to sequencing and subsequent analysis in order to determine whether a genuine fragment of a cystathionine γ-lyase homologue had been amplified from the *T. vaginalis* cDNA.

EXAMPLE 4

Isolation of Full Length *T. vaginalis* Homocysteine Desulphurase Genes

Two PCR clones (designated cysta 2 and cysta 16) were used to isolate the corresponding full length genes from a *T. vaginalis* λZAP II cDNA library (Mallinson, D. J, Lockwood, B. C., Coombs, G. H., North, M. J. (1994). Identification and molecular cloning of four cysteine proteinase genes from the pathogenic protozoan *Trichomonas vaginalis*. J. Gen. Microbiology 140 2725–2735). A total of 100,000 cDNA clones were screened according to the following procedure. 100,000 bacteriophage were plated in L-top agarose, along with the host cells *E. coli* XL1 blue and the bacteriophage plaques were allowed to propagate at 37° C. until they were just touching one another in the bacterial lawn. The bacteriophage plaques were then transferred by blotting onto a Hybond N nylon filter (available from Amersham, Little Chalfont, Bucks, UK).

The DNA of the bacteriophage was denatured in situ and subsequently hybridised with either the cysta 2 or cysta 16 200 base pair homocysteine desulphurase fragments, radioactively labelled by random priming.

Primary screening of the cDNA library, using conditions of high stringency, 1 hr in 0.1×SSC/0.1% SDS at 65° C., revealed that 25 plaques hybridised with the cysta 2 probe, whilst 18 hybridised with the cysta 16 probe. Autoradiographic film showing the positively hybridising plaques was aligned with the plates containing the bacteriophage in order to allow plugs of agarose containing the positive bacteriophage to be removed. The plugs were placed into SM buffer and a trace of chloroform at 4° C. and the phage allowed to defuse out overnight.

A second round of bacteriophage purification was carried out in order to identify individual plaques which hybridised under high stringency conditions with either the cysta 2 or cysta 16, 200 base pair radioactive probe.

EXAMPLE 5

Analysis of Cysta 2 and Cysta 16 Hybridising Clones

Two λ clones which hybridised with the cysta 2 probe and five λ clones which hybridised with the cysta 16 probe were rescued directly into pBluescript using the F1 helper bacteriophage mechanism (according to the manufacturers instructions, Stratagene, La Jolla, Calif., USA, protocols). The rescued plasmids were subsequently analysed by restriction analysis to determine the sizes of cloned insert DNA.

As a result of the restriction analysis of the plasmids isolated with the cysta 2 or cysta 16 probes, two clones, one a cysta 2 hybridiser (ctlα, subsequently renamed as mgl1) and the other a cysta 16 hybridiser (ctlβ subsequently renamed as mgl2), were chosen to be fully sequenced. These two clones were chosen as they had the largest inserts (approximately 1.2 to 1.3 kilobases in size) and were thought to be of sufficient size to encode a full length copy of the a homocysteine desulphurase gene from *T. vaginalis*.

EXAMPLE 6

Sequencing of Two *T. vaginalis* Homocysteine Desulphurase Genes

Restriction mapping of each of the two *T. vaginalis* homocysteine desulphurase genes was carried out in order to allow subcloning of smaller fragments that would assist in obtaining the full nucleotide sequence of each gene.

Sequencing of the two clones and their respective subclones was achieved using Sequenase$^{(RTM)}$ quick Denature Plasmid sequencing kit (available from Amersham, Little Chalfront, Bucks, UK) with T7 and T3 primers (available from Stratagene, LA Jolla, Calif., USA) according to the manufacturer's instructions. The complete nucleotide sequence and predicted amino acid sequence of the first clone (mgl1) (SEQ ID NO:1 and SEQ ID NO:2) and the complete nucleotide sequence and predicted amino acid sequence of the second clone (mgl2) (SEQ ID NO:2 and (SEQ ID NO:3) was determined.

In order to obtain the 5' untranslated regions (UTRs) of mgl1 and mgl2 and to confirm the start codons, 5' Reverse Transcriptase Rapid Amplification of cDNA ends (RT-RACE) was performed using the commercially available 5' RACE kit (available from Gibco, Paisley, Scotland) according to the manufactures instructions. Both the mgl1 and mgl2 RACE products which were obtained were approximately 250 base pairs in size. The mgl1 and mgl2 RACE products were cloned directly into a pTAg vector of the ligATor kit (available from R & D Systems, Minneapolis, USA), according to the manufacturer's instructions. This system exploits the feature that PCRs performed in the presence of Taq polymerase have a 5' adenosine overhang tagged onto the ends of any amplified fragments. The system facilitates the cloning of PCR products into a vector which has a complementary thymidine residue overhang.

Restriction analysis of the transformants revealed that the 5' RACE products had been cloned into the pTAg vector. Sequencing of the RACE clones was carried out on both strands using commercially available −20 primer and M13 reverse primer.

Sequencing of the 5' RACE product of mgl1 revealed that the 5' UTR is very short (13 nucleotides long), but confirmed the start ATG codon identified from the cDNA sequence.

Two independent 5' RACE products were obtained for mgl2, both clones possessed the ATG start codon which was absent from the copy of the gene isolated from the cDNA library. The longer mgl2 RACE clone identified a short 5' UTR region of some 14 nucleotides in length.

Both the mgl1 and mgl2 5' UTRs are shown together with the respective complete cDNA sequence and predicted amino acid sequences of mgl1 and mgl2 in FIGS. 1 and 2. Pileup analysis (see Table 1) revealed the relatively low level of sequence identity of the putative MGL1 and MGL2 to previously sequenced cystathionine γ-lyases and that it was unlikely that a *T. vaginalis* cystathionine γ-lyases had been cloned. This was confirmed by the finding that the cloned gene products do not have cystathionine γ-lyase activity (see Table 2).

EXAMPLE 7

Cloning and Expression of Histidine-Tagged Homocysteine Desulphurase Fusion Protein The QIAexpress system (Qiagen, La Jolla, Calif., USA) was used for the expression and purification of MGL1 and MGL2 polypeptides. The mgl1 and mgl2 genes were cloned into a pQE vector which encodes a 6-Histidine tag at the N or C terminus of the expressed protein. The 6-Histidine tagged protein is then affinity purified using a $Ni^{2+}$-NTA resin (see QIAexpress handbook for details).

Cloning of mgl1

The mgl cDNA clone was maintained in the pasmid pBluescript. Preliminary sequence analysis indicated that the *T. vaginalis* mgl1 cDNA had been cloned into pBluescript in the reverse orientation to what was expected, therefore direct subcloning of mgl1 from pBluescript to a pQE vector was not possible. In order to overcome the problems of the orientation of mgl1 cDNA in pBluescript, a PCR cloning strategy was adopted to enable the cDNA to be cloned into an appropriate pQE vector.

Oligonucleotide primers were designed to the 5' and 3' ends of the mgl1 cDNA which included the restriction endonuclease sites NcoI and BglII, respectively. Through the PCR amplification process these two restriction sites were engineered on to the ends of the mgl1 DNA, their presence facilitating cloning of DNA into NcoI and BglII restricted pQE vector. The nucleotide sequence of the two primers are shown in FIG. 5 (SEQ ID NO:22 and SEQ ID NO:23).

pQE 60, a type ATG construct was chosen as the vector into which the mgl1 DNA was to be cloned. The ATG construct allows the expressed protein to start with the authentic ATG codon. The mgl1 cDNA encoded a start methionine and was therefore considered suitable for cloning into this particular pQE vector (see QIA express handbook for details).

pBluescript containing mgl1 cDNA was linearised using BamHI and the linearised DNA was used as the template for PCRs along with the two oligonucleotides outlined in FIG. 5. The components of the PCR mix are outlined below.

1 μl (10 ng/μl) pBluescript/mgl1 BamHI linearised template
5 μl (100 ng/μl) 5' NcoI primer
5 μl (100 ng/μl) 3' BglII primer
5 μl 10× pfu buffer (Stratagene, La Jolla, Calif., USA)
2.5 μl 5 mM each of dATP, dGTP, dCTP, dTTP
1 μl pfu polymerase (a proofreading version of Taq available from Stratagene, La Jolla, Calif., USA)
30.5 μl water Amplification of the mgl1 DNA was performed using the conditions outlined below.
94° C. for 5 minutes followed by 30 cycles of 94° C. for 1 minute,
42° C. for 1 minute, and
72° C. for 1 minute and finally a single extension reaction of 72° C. for 5 minutes After amplification by PCR, contaminating nucleotides and polymerase were removed from the mgl1 DNA using Magic PCR Wizard preps (Promega, Madison, Wis., USA) according to the manufactures instructions. The cleaned up mgl1 DNA which now possessed an NcoI site at its 5' end and a BglII site at its 3' end was restricted with these two enzymes as was the pQE60 vector. The restricted pQE vector and mgl1 DNA were ligated and intact vector containing insert was transformed into M15[pREP4] cells, see QIAexpress handbook for details. pQE 60 plasmid containing mgl1 DNA was then used for test expression of recombinant protein according to the QIAexpress handbook.

Cloning of mgl2 mgl2 cDNA contained within pBluescript was subcloned directly into pQE30. pBluescript containing mgl2 DNA was restricted with BamHI and XhoI and this restricted insert was ligated with pQE30 vector that had been restricted with BamHI and SalI. Intact pQE30 vector and insert was transformed into M15 pREP4 cells. pQE 30 vector containing mgl2 DNA was then used for test expression of recombinant protein according to the QIAexpress handbook.

The pQE plasmids containing either mgl1 or mgl2 were transformed into *E. coli* strain M15[pREP4] and single colonies obtained. A single colony was inoculated into 20 ml LB-both containing 100 ug/ml ampicillin and 25 ug/ml kanamycin grown overnight at 37° C.

1 liter of LB-broth was then inoculated with the entire overnight culture and then culture grown at 37° C. until $A_{750}$ reached 0.8 (approximately 2–3 hours). IPTG was then added to a final concentration of 1 mM and growth was allowed to continue at 37° C. for a further 2½ hours.

The cells were harvested by centrifugation and frozen at –70 C.

Expressed protein was purified by FPLC using a metal chelating resin, such as Ni-NTA superflow, according to protocol 5 of the Qiagen QIAexpress protocols.

Protein-containing fractions obtained by FPLC were analysed by SDS-PAGE and those with recombinant homocysteine desulphurase were combined and dialysed overnight against sonication buffer (50 mM Na-phosphate pH 8.0, 300 mM NaCl) containing 10% glycerol before storage at –20° C.

EXAMPLE 8

Modified Procedure for the Purification of Recombinant *T. vaginalis* Homocysteine Desulphurase The procedures detailed below encompass growth of bacteria, expression of recombinant enzyme and FPLC/Ni-NTA purification. Details of all buffers, media etc are given in the appendix. Additional details of vector, bacterial host strain and protocols can be found with reference to the QIAGEN protein expression handbook.

Day 1

Streak out 5 μl of the supplied glycerol stock of M15 [pREP4] cells (containing pQE30/*T. vaginalis* cDNA) onto Luria-Bertani (LB) agar plates containing ampicillin (100 μg/ml) and kanamycin (25 μg/ml). Grow up overnight @ 37° C. [Colonies on LB plates can be stored at 4° C. for up to 2 weeks].

Day 2

In a 500 ml flask inoculate 50 ml of LB broth containing ampicillin and kanamycin (final concentrations as above) with a single colony. Grow up overnight at 37° C. with shaking—200 rpm in an orbital shaker.

Day 3

In a 2 liter flask, inoculate 400 ml of fresh LB broth plus ampicillin and kanamycin with the 50 ml overnight culture.

Grow the culture for 1.75 h with shaking (200 rpm) at 37° C. Induce the cells to express homocysteine desulphurase by addition of sterile IPTG (to give a final concentration of 0.2 mM) and grow for a further 2.25 h with shaking at 37° C.

Pellet the cells by centrifugation at 8000 g at 4° C. for 10–15 min.

Resuspend the pellet in 5 ml of sonication buffer and transfer to a 15 ml Falcon tube, add pyridoxal 5' phosphate (PLP) to a final concentration of 20 $\mu$M. Freeze the resuspended cells at −70° C. until required for purification. N.B. To check that expression has worked, 200 $\mu$l samples of bacterial culture are removed a) just before addition of IPTG and b) after the addition of IPTG, at the end of the 2.25 h induction period. The cells are pelleted (13000 rpm/5 min), resuspended in 80 $\mu$l of Laemmli's sample buffer, boiled for 5 min, and a 10 $\mu$l aliquot run on a 12.5% SDS-PAGE gel to confirm expression of homocysteine desulphurase after induction by IPTG. [Alternatively a larger volume of uninduced and induced cells (1 ml) may be sampled, lysed by sonication and a homocysteine desulphurase activity assay carried out].

Equilibrate Ni-NTA resin column overnight with sonication buffer. Typically 8 ml packed volume of resin/column may be used.

Day 4 Affinity purification of His-tagged enzyme on Ni-NTA resin by FPLC.

1. Remove frozen cells from −70° C. freezer, thaw by placing the tube in a beaker of cold water.

2. Lyse the cells by sonication.

3. Transfer the sonicated material to a 50 ml centrifuge tube and centrifuge at 10,000 g for 30 min at 4° C. It is useful to check that the bacteria have been lysed adequately, especially when first using a sonicator, by comparing pellet and supernatant fractions by SDS-PAGE. Homocysteine desulphurase is highly soluble and 95% should be found in the soluble fraction.

4. After centrifugation, the supernatant [which contains the soluble enzyme](~5-6 ml total vol.) is filtered through a 0.22 $\mu$m Millipore filter directly into a Luer-lock lock syringe attached to the priming nozzle (injection port) of the FPLC and the purification started.

Note: The purification procedure outlined was performed on a Waters FPLC system including a Waters 600S controller and Waters 626 pump. The basic steps are: sample application (the sample is automatically drawn from the syringe onto the column when the priming nozzle is turned to 'injection' mode). The enzyme can actually be seen to bind to the NI-NTA resin, as a very bright yellow band.

1. short wash with sonication buffer
2. longer wash with wash buffer
3. elution of enzyme using a linear gradient 0–500 mM imidazole [100% wash buffer to 100% elution buffer (inc. 500 mM imidazole)]

Note: for full details of FPLC running conditions (flow rates, durations of washes, gradients etc.) see appendix.

5. The protein concentration in the column outflow is monitored continuously by a UV detector set at 280 nm, and fractions are collected throughout the procedure.

6. Fractions containing recombinant enzyme (easily identified by their bright yellow-green colour) are pooled and dialysed against 1 liter of dialysis buffer overnight (with several changes if necessary) at 4° C. (to remove the imidazole).

7. A small sample (~50 $\mu$l) of the dialysed enzyme preparation is taken for determination of the protein content using the BCA procedure (Pierce Chemical Company BCA [Bicinchoninic acid] reagent kit). The remainder of the preparation is combined 1:1 with stabilisation buffer, and stored in 1 ml aliquots @ −20° C.

APPENDIX

Reagents and buffers required.

Luria-Bertani Medium (LB medium)

| For 1 litre : Dissolve the following in 950 ml $H_2O$ : | |
| --- | --- |
| bacto-tryptone | 10 g |
| bacto yeast extract | 5 g |
| NaCl | 10 g |

Adjust pH to 7.0 (if necessary). Make to 1 l with dist. $H_2O$. Sterilise by autoclaving for 20 min. @ 15 lb/sq. in. (For LB agar, include 15 g of bacto agar per liter).

Antibiotics

Ampicillin (Sigma A-9518)

(100 mg/ml stock in distilled $H_2O$)—sterilised by filtration through a 0.2 $\mu$m Millipore filter, stored as 1 ml aliquots @ −20° C.

Kanamycin (Sigma K-4000)

(25 mg/ml stock in dist. $H_2O$)—sterilised and stored as above.

IPTG (isopropyl-$\beta$-D-thiogalactopyranoside; Gibco BRL 15529-019)

1 M stock (in dist. $H_2O$)—filter sterilised (0.2 $\mu$m filter), stored in 1 ml aliquots @ −20° C.

Pyridoxal 5'-phosphate (PLP; Sigma P-9255)

1 mM stock in dist. $H_2O$. Make up fresh each time (for addition to resuspended cells).

Ni-NTA Superflow resin (QIAGEN 30430) Sonication buffer: 50 mM sodium phosphate buffer, pH 8.0, 300 mM NaCl 1 M $Na_2HPO_4$: 46.6 ml
1 M $NaH_2PO_4$: 3.4 ml
17.53 g NaCl Make to 1 liter with dist. $H_2O$.

Wash buffer: 50 mM sodium phosphate buffer, pH 6.0, 300 mM NaCl, 10% glycerol

1 M $Na_2HPO_4$: 6 ml
1 M $NaH_2PO_4$: 44 ml
17.53 g NaCl
100 ml glycerol

Make to 1 l with dist. $H_2O$

Elution buffer: wash buffer containing 500 mM imidazole

Dissolve 17.02 g imidazole in 500 ml wash buffer. (Imidazole-Sigma I-O125)

Dialysis buffer: 100 mM sodium phosphate buffer, pH 6.5, 300 mM, 20% glycerol, 20 $\mu$M PLP, 15 $\mu$M dithiothreitol 1 M $Na_2HPO_4$: 30.35 ml
1 M $NaH_2PO_4$: 69.65 ml
17.53 g NaCl
200 ml glycerol
2 ml of 10 mM PLP stock
15 $\mu$l of 1 M dithiothreitol stock (dithiothreitol-Sigma D-9779)

Stabilisation buffer: 100 mM sodium phosphate buffer pH 6.5, 80% glycerol, 40 µM PLP, 30 µM DTT For 10 ml: 1.96 ml of 100 mM sodium phosphate buffer, pH 6.5 8 ml glycerol, 40 µl of 10 mM PLP, 3 µl of 100 mM DTT Sodium azide (Sigma S-2002): 0.05% solution pump onto Ni-NTA column after use to prevent bacterial growth (store column in azide @ 4° C. between purifications).

Make 10% (w/v) stock in dist. $H_2O$ (store @ 4° C.). Dilute to give 0.05% working concentration.

All buffers used on FPLC should be degassed prior to use Degassing achieved by filtration of buffer through a 0.2 µm filter using a Millipore vacuum filter unit.

Homocysteine desulphurase activity assay used to monitor purification

Homocysteine→2-ketobutyrate+$NH_3$+$H_2S$

The assay measures the production of $H_2S$; $H_2S$ is 'trapped' by lead acetate forming colloidal lead sulphide (a deep brown coloured compound) which has maximal absorbance at 360 nm.

Reagents

Assay buffer: 100 mM imidazole buffer, pH 6.5

D,L-homocysteine (Sigma H-4628); stock solution 100 mM (made up in assay buffer). Final concentration in assay=40 mM (400 µl of stock)

Lead acetate (BDH 10142); stock solution 3.3 mM (made up in dist. $H_2O$). Final concentration in assay=0.33 mM (100 µl of stock)

Recombinant enzyme: as a start point, use 10 µl of a 100× dilution of the pure enzyme prep. (dilute enzyme prep. in 100 mM sodium phosphate buffer, pH 6.5)

Final volume of assay mixture is made up to 1.0 ml with assay buffer.

Run control assay mixtures: 1) minus enzyme, 2) minus substrate.

Calculation of enzyme activity

Use molar extinction coefficient for lead sulphide of 5205 $M^{-1}$ $cm^{-1}$.

$$\frac{\text{change in abs}_{(exp\mu)} - \text{change in abs.}_{(control)} \times 10^6}{\text{time} \times \text{protein concentration} \times 5205\ M^{-1}\ cm^{-1} \times 10^3} =$$

$\mu$ moles $min^{-1}$ mg $prot^{-1}$

Details of FPLC programme for purification of recombinant *T. Vaginalis* MGL2

| | | GRADIENT | | |
|---|---|---|---|---|
| TIME | FLOW | % A | % B | % C |
| 1. (Sample applied 0–30 min) | 0.2 | 100 | 0 | 0 |
| 2. 30 | 0.5 | 100 | 0 | 0 |
| 3. 90 | 0.5 | 0 | 100 | 0 |
| 4. 150 | 0.5 | 0 | 100 | 0 |
| 5. 250 | 0.5 | 0 | 0 | 100 |

Buffers:
A = Sonication buffer
B = Wash buffer
C = Elution buffer

EXAMPLE 9

Homocysteine Assays

ASSAY I

Homocysteine levels were measured using recombinant homocysteine desulphurase prepared according to the previous examples in 66 mM sodium phosphate buffer pH 7.5, 0.33 mM lead acetate.

Homocysteine desulphurase catalyses the conversation of homocysteine to α-ketobutyrate, ammonia and hydrogen sulphide. The hydrogen sulphide reacts with lead acetate to produce lead sulphide which can be detected spectrophotometrically at 360 nm (Molar extinction coefficient=5205 $M^{-1}$ $cm^{-1}$).

| assay reagents | |
|---|---|
| 0.1 M sodium phosphate | 0.5 ml |
| 1 mM lead acetate | 0.5 ml |
| homocysteine 100 µM to 10 mM (33 µM–3.3 mM final concentration) | 0.49 ml |
| homocysteine desulphurase (6 µg/ml) -added last | 10 µl |

The assay was incubated at 20° C. for 0 to 120 minutes to allow the colour to develop. The homocysteine levels were then determined by measuring the absorbance at 360 nm.

| Results | |
|---|---|
| homocysteine concentrations | change in absorbance (40 min) |
| 3.3 mN | 1.066 |
| 333 µM | 0.790 |
| 33 µM | 0.06 |

ASSAY II

Assay Principle

Dithiothreitol (DTT) is initially used to break homocysteine down into homocysteine and to release protein bound homocyst(e)ine. The homocysteine is then broken down into α-ketobutyrate, $NH_3$ and $H_2S$ by the action of homocysteine desulphurase. A specific lactate dehydrogenase isoenzyme is then utilised to convert α-ketobutyrate into α-hydroxybutyrate with the concomitant release of $NAD^+$. After removal of any NADH by lowering of the pH using HCl the NAD is fed into a cycling mechanism involving ethanol, alcohol dehydrogenase, diaphorase and tetrazolium salts to generate a coloured product which can be photometrically measured. The increase in colour corresponds to the concentration of homocysteine in the sample.

Performance of the assay

Step 1: Mix 100 µl of sample (e.g citrated plasma) with 500 ul 0.1 mol/l HEPES, 0.1 mmol/l NADH, 20,000 µmoles/min/l homocysteine desulphurase, 50,000 U/l Lactate dehydrogenase and 0.5 mol/l dithiothreitol, pH 8.0 into a cuvette. Incubate at 37° C. for 20 min.

Step 2: Add 500 ul 1 mol/l HCl, 0.55% (v/v) Nonidet P40, $1 \times 10^{-4}$ mol/l nitroblue tetrazolium (NBT). Incubate at 37° C. for 5 min.

Step 3: Add 500 ul tris (hydroxymethylaminomethane) (TRIS), 1 mol/l ethanol followed by 50 ul 20,000 U/l alcohol dehydrogenase, 1000 U/l diaphorase.

Measure the increase in absorbance at 527 nm for 5 minutes after the addition of the reagent containing alcohol dehydrogenase.

Assay performance
i) standard curve
A typical standard curve is shown in the table below:

| Homocysteine concentration (µmol/l) | Delta Abs. 527 nm/10 min |
|---|---|
| 0 | 0.385 |
| 10 | 0.495 |
| 20 | 0.580 |
| 30 | 0.670 |
| 40 | 0.770 |
| 50 | 0.850 |

Standard curve was generated by spiking homocysteine into serum. The background signal is in part caused by endogenous levels of homocysteine ii) Sensitivity It is clearly possible to detect concentrations of <5 µmol/l homocysteine.

iii) Recovery

Homocysteine was spiked into plasma and the recovery determined:

| Homocysteine added (µmol/l) | Homocysteine recovered (µmol/l) | % recovery |
|---|---|---|
| 25 | 20.7 | 83 |
| 50 | 53.2 | 106 |
| 75 | 65.5 | 87 |
| 100 | 95.7 | 96 | iv) Linearity

The following table illustrates the linearity of the response:

| Amount of saline added (%) | Measured delta Abs. 527 nm/10 min | Theoretical delta Abs. 527 nm/10 min | Signal as percent of expected signal |
|---|---|---|---|
| 0 | 0.52 | 0.52 | 100% |
| 10 | 0.45 | 0.47 | 95.7% |
| 20 | 0.41 | 0.42 | 97.6% |
| 30 | 0.35 | 0.37 | 94.6% |
| 40 | 0.3 | 0.31 | 96.8% |
| 50 | 0.22 | 0.26 | 84.6% |
| 100 | 0 | 0 | — |

A patient sample (plasma) was diluted using the above amounts of saline and the measured signal compared to the theoretical signal.

v) Cross reactivity

The following table illustrates the cross reactivity of the assay with methionine and cysteine:

| Concentration of analyte (µmoles/l) | Delta Abs. 527 nm/10 min | | |
|---|---|---|---|
| | Homocysteine | Methionine | Cysteine |
| 0 | 0.52 | 0.52 | 0.52 |
| 25 | — | 0.51 | 0.48 |
| 50 | — | 0.52 | 0.5 |
| 100 | — | 0.49 | 0.51 |
| 200 | 1.1 | 0.5 | 0.49 |

Homocysteine, methionine and cysteine were spiked into plasma and the signal measured. No cross reactivity with either cysteine or methionine was observed up to levels of 200 µmols/l.

EXAMPLE 10

Site-Directed Mutagenesis of Recombinant MGL1 and MGL2

The production of mutated rMGL1 (C113G) and rMGL2 (C116G) was achieved using the PCR-based QuikChange™ Site-Directed Mutagenesis kit (Stratagene). Double-stranded mgl1 and mgl2 cDNAs (in either p-Bluescript or pQE30/60 expression vectors) were used as templates. Mutagenesis was performed using a pair of oligonucleotide primers complementary to opposite strands of the cDNA clones, each containing a point mutation to convert the respective cysteine codons (TGC) to glycine codons (GGC), as follows: 1) 5'-TGCCTTTATGGC GGCACATGCTCTCT-3' (SEQ ID NO:9); 2) 5'-AAGAGAGCATGTGTGCCGCCATAAAGG-3' (SEQ ID NO:10). Following PCR-mediated amplification of mutated cDNAs, the original template cDNAs/vectors were selectively digested using the Dpn-I endonuclease. cDNA clones containing the desired mutations were identified by sequencing on both strands using gene specific oligonucleotide primers. cDNAs mutated in p-Bluescript were subcloned into pQE vectors prior to expression. Production and purification of recombinant mutated MGL1 and MGL2 was performed as described previously.

EXAMPLE 11

Enzymatic Studies of Recombinant MGL1 (SEQ ID NO:2), and MGL2 (SEQ ID NO:4), and mutated MGL1 (C113G) (SEQ ID NO:6) and MGL2 (C116G) (SEQ ID NO:8)

Methionine γ-lyase previously purified from *T. vaginalis* has activity towards a number of substrates, including methionine, homocysteine and S-adenosylmethionine, but has no activity towards cystathionine (Lockwood and Coombs, 1991). In order to assess the similarity between MGL1 and MGL2 and purified native methionine γ-lyase, the enzyme activities of the recombinant enzymes were analysed (Table 2). rMGL1 and rMGL2 were found to have very high activity towards homocysteine, and also to catabolise methionine, cysteine and O-acetylserine rapidly. The two recombinant enzymes were unable to utilise cystathionine as a substrate. The kinetic parameters of the two recombinant proteins were also determined for homocysteine and cysteine (Table 3). The apparent $K_m$ of rMGL1 for the two substrates was higher than those for rMGL2, the largest difference being for methionine.

Following production and purification of mutated rMGL1 (C113G) and rMGL2 (C116G), their enzymatic activities were compared with those of the corresponding wild-type enzymes (Table 2). Under optimal conditions the activities of rMGL1 (C113G) towards all substrates were considerably lower than those of wild-type rMGL1, rMGL2 (C116G) also had lower activities towards homocysteine and methionine than wild-type rMGL2, but surprisingly the activity of the mutated enzyme towards cysteine and O-acetyl-L-serine was increased. Neither of the mutated enzymes exhibited activity towards cystathionine.

Comparative kinetic analyses of the mutated and wild-type enzymes with respect to the catabolism of homocysteine and cysteine were performed (Table 3). The slightly higher $K_m$ and markedly lower $V_{max}$ values of rMGL1 (C113G) compared with those of wild-type rMGL1 suggest reduced substrate binding efficiency of this mutated enzyme. In contrast, the apparent $K_m$ of rMGL2 (C116G) for cysteine was considerably lower than that of rMGL2, and this correlates with the enhanced activity (higher $V_{max}$) of the mutated enzyme towards this substrate. Unexpectedly the $K_m$ of rMGL2 (C116G) for homocysteine was also much reduced relative to that of the wild-type enzyme, despite the significantly lower $V_{max}$ of the mutated enzyme towards this substrate.

TABLE 2

Comparison of enzymatic activities of mutated and wild-type recombinant proteins

| Substrate | rMGL1 | rMGL1(C113G) | mutant/wildtype (%) |
|---|---|---|---|
| Homocysteine | 370 ± 11 (8) | 34.5 ± 3.2 (14) | 9.3 |
| Methionine | 10.4 ± 0.31 (4) | 0.79 ± 0.17 (8) | 7.6 |
| Cysteine | 6.02 ± 0.63 (8) | 2.33 ± 0.35 (8) | 38.7 |
| O-acetyl-L-serine | 3.74 ± 0.1 (4) | 1.83 ± 0.12 (8) | 48.9 |
| Cystathionine | N.D (4) | N.D (8) | — |

| Substrate | rMGL2 | MGL2(C116G) | mutant/wildtype (%) |
|---|---|---|---|
| Homocysteine | 128 ± 22 (14) | 27.0 ± 5.8 (19) | 21.2 |
| Methionine | 0.67 ± 0.18 (11) | 0.15 ± 0.05 (14) | 22.4 |
| Cysteine | 1.06 ± 0.42 (16) | 2.31 ± 0.71 (17) | 217.9 |
| O-acetyl-L-serine | 1.51 ± 0.49 (12) | 2.15 ± 0.17 (14) | 142.4 |
| Cystathionine | N.D (12) | N.D (8) | — |

Activities (in $\mu$mol min$^{-1}$ mg protein$^{-1}$) are means ±S.D. from the number of experiments given in parentheses. Activity towards homocysteine and cysteine was assayed by monitoring hydrogen sulphide production using the standard procedure; activity towards the other substrates was measured via the standard α-keto acid production assay. N.D., activity not detectable (<0.04 $\mu$mol min$^{-1}$ mg protein$^{-1}$).

TABLE 3

Kinetic parameters of wild type and mutated rMGL1 and rMGL2 with respect to catabolism of homocysteine and cysteine

| | Homocysteine | | Cysteine | |
|---|---|---|---|---|
| | $K_M^1$ | $V_{max}^2$ | $K_m^1$ | $V_{max}^2$ |
| rMGL1 | 12.2 | 256 | 8.5 | 14.9 |
| rMGL1 (C113O) | 15.2 | 42 | 9.7 | 4.6 |
| rMGL2 | 37.7 | 132 | 22.3 | 2.4 |
| rMGL2 (C116G) | 6.2 | 53 | 3.6 | 4.8 |

At least 10 different substrate concentrations were used, with at least 3 replicate assays. $^1$mM, $^2\mu$mol min$^{-1}$ mg protein$^{-1}$.

REFERENCES

1. Ueland, P. M. (1992) Plasma homocysteine and cardiovascular disease. In: Athersclerotic cardiovascular disease (Francis, R. N. ed.), pp. 183–230. Marcel Decker. New York.
2. Kluijtmans, L. A. J, et al. (1996) Molecular genetic analysis of mild hyperhomocysteinemia: A common mutation in the methylenetetrahydrofolate reductase gene is a genetic risk factor for cardiovascular disease. Am.J.Hum.Genet.58, 35.
3. Cravo, M. L. et al. (1996) Hyperhomocysteinemia in chronic alcoholism: correlation with folate, vitamin B-12 and vitamin B-6 status. Am.J.Clin.Nutr.63,220.
4. Bostom, A. G. et al (1996) High dose B-vitamin treatment of hyperhomocysteinemia in dialysis patients, Kidney International 49, 147.
5. Steegers-Theunissen, R. P. M. (1992) Hyperhomocysteinaemia and recurrent spontaneous abortion or abruptioplacentae. Lancent 339, 1122.
6. Mudd, S. H. (1989) Disorders of transsulphuration. In: The metabolic basis of inherited disease (Scriver, C. R. ed.) pp. 693–734. McGraw-Hill. New York.
7. te Poele-Pothoff, M. T. W. B. et al (1995) Three different methods for the determination of total homocysteine in plasma. Ann.Clin.Biochem. 32, 218.
8. Hori, H., Takabayashi, K., Orvis, L., Carson, D. A., Nobori, T. (1996) Gene cloning and characterisation of *Pseudomonas putida* L-methionine-alpha-deamino-gamma-mercaptomethane-lyase. Cancer Research 56 No. 9 pp 2116– 2122.
9. Sambrook, J., Fritsch, E. F. and Maniatis, T. (1989) Molecular Cloning, A laboratory manual (2nd ed.). Cold Spring Harbor Laboratory Press.
10. Ono, B. I., Tanaka, K., Naito, K., Heike, C., Shinoda, S., Yamamoto, S., Ohmori, S., Oshima, T. and Toh-E, A. (1992) Cloning and characterization of the CYS3 gene of *Saccharaomyces cerevisiae. Journal of Bacteriology* 174, 3339–3347.
11. Lu, Y., O'Dowd, B. F., Orrego, H. and Israel, Y. (1992) Cloning and nucleotide sequence of human liver cDNA encoding for cystathionine γ-lyase. *Biochemical and Biophysical Research Communications* 189, 749–758.
12. Lockwood, B. C. and Coombs, G. H (1991) Purification and characterisation of methionine γ-lyase from *Trichomonas vaginalis. Biochemical Journal.* 279, 675–682.
13. Erickson, P. F., Maxwell, I. H., Su, L. J., Baumann, M. and Glode, L. M. (1990) Sequence of cDNA for cystathionine γ-lyase and comparison of deduced amino acid sequence with related *Escherichia coli* enzymes. *Biochemical Journal* 269, 335–340.
14. Lockwood, B. C., North, M. J. and Coombs, G. H. (1984) *Trichomonas vaginalis, Tritrichomonas foetus* and *Trichomitus Batrachorum:* Comparative proteolytic activity. Experimental Parasitology 58, 245–253.

What is claimed is:

1. A method of assaying homocysteine in a sample, comprising the steps of:
   contacting the sample with an enzyme capable of degrading homocysteine, and
   determining any reaction product(s) formed by enzyme degradation of homocysteine by said enzyme.

2. The method of assaying homocysteine according to claim 1 wherein the enzyme is homocysteine desulphurase.

3. The method of assaying homocysteine according to claim 2 wherein the homocysteine desulphurase is a recombinant protozoan homocysteine desulphurase or functionally active derivative thereof displaying homocysteine desulphurase activity.

4. A method of assaying homocysteine according to claim 2 wherein the homocysteine desulphurase has an amino acid sequence substantially similar to a sequence selected from SEQ ID NO:2, SEQ ID NO:4, SEQ ID NO:6 and SEQ ID NO:8.

5. A method of assaying homocysteine according to claim 1 wherein one of said reaction product(s) is α-ketobutyrate and a level of α-ketobutyrate is determined.

6. A method of assaying homocysteine according to claim 1 wherein one of said reaction product(s) is hydrogen sulphide and a level of hydrogen sulphide is determined.

7. A method of assaying homocysteine according to claim 1 wherein one of said reaction products is ammonia and a level of ammonia is determined.

8. The method of assaying homocysteine according to claim 5 wherein the level of -ketobutyrate is determined by reacting the α-ketobutyrate with NADH and lactate dehydrogenase or pyruvate dehydrogenase so as to convert the α-ketobutyrate to a α-hydroxybutyrate with the generation of $NAD^+$ and determining a level of $NAD^+$.

9. A method of assaying homocysteine according to claim 1 wherein said method is sensitive enough to detect a concentration of <5 µmol/l homocysteine.

10. A method of assaying an analyte degradable to homocysteine, which comprises first degrading the analyte to homocysteine and then estimating the homocysteine produced by the method of claim 1.

11. The method according to claim 10 wherein the analyte is homocysteine or methionine.

12. A method of assaying methionine, cysteine or O-acetyl-L-serine in a sample comprising the steps of:
   a) contacting the sample with recombinant protozoan homocysteine desulphurase or functionally active derivative thereof capable of degrading methionine, cysteine or O-acetyl-L-serine, and
   b) determining any reaction product(s) formed by enzyme degradation of methionine, cysteine or O-acetyl-L-serine.

13. A kit for diagnostic in vitro determination of a homocysteine level in a sample, wherein the kit comprises:
   a) an enzyme capable of degrading homocysteine, and
   b) means for enabling determination of reaction products produced by degradation of homocysteine by the enzyme.

14. The kit for diagnostic in vitro determination of a homocysteine level in a sample according to claim 13 wherein the enzyme is homocysteine desulphurase.

15. The kit for diagnostic in vitro determination of a homocysteine level in a sample according to claim 14 wherein the homocysteine desulphurase is a recombinant protozoan homocysteine desulphurase or functionally active derivative thereof displaying homocysteine desulphurase activity.

16. A kit for diagnostic in vitro determination of a homocysteine level in a sample according to claim 14 wherein the homocysteine desulphurase has an amino acid sequence substantially similar to a sequence selected from SEQ ID NO:2, SEQ ID NO:4, SEQ ID NO:6, and SEQ ID NO:8.

17. A polynucleotide fragment encoding a protozoan homocysteine desulphurase.

18. The polynucleotide fragment according to claim 17 wherein the polynucleotide fragment is a deoxyribose nucleic acid (DNA) fragment.

19. A polynucleotide fragment according to claim 17 where said polynucleotide fragment encodes a polypeptide having an amino acid sequence substantially similar to a sequence selected from SEQ ID NO:2, SEQ ID NO:4, SEQ ID NO:6, and SEQ ID NO:8 or a functionally active derivative thereof.

20. A polynucleotide fragment according to claim 17, said polynucleotide having a nucleotide sequence substantially the same as a sequence selected from SEQ ID NO:1, SEQ ID NO:3, SEQ ID NO:5, and SEQ ID NO:7.

21. A recombinant nucleic acid molecule comprising a polynucleotide fragment according to claim 17.

22. A recombinant nucleic acid molecule according to claim 21 characterised in that the recombinant nucleic acid molecule comprises regulatory control sequences operably linked to said polynucleotide fragment for controlling expression of said polynucleotide fragment.

23. A recombinant nucleic acid molecule according to claim 21 wherein the recombinant nucleic acid molecule is a plasmid.

24. A recombinant nucleic acid molecule according to claim 21 wherein the recombinant nucleic acid molecule is derived from a viral vector.

25. A prokaryotic or eukaryotic host cell transformed by a polynucleotide fragment or recombinant molecule according to claim 17.

26. A recombinant protozoan homocysteine desulphurase polypeptide or functionally active derivative thereof displaying homocysteine desulphurase activity.

27. A homocysteine desulphurase polypeptide having an amino acid sequence selected from SEQ ID NO:2, SEQ ID NO:4, SEQ ID NO:6, and SEQ ID NO:8 or a functionally active derivative thereof.

28. An antibody immuno-reactive with a polypeptide or fragment according to claim 27.

29. A polynucleotide fragment according to claim 17 for use in therapy.

30. A recombinant nucleic acid molecule according to claim 21 for use in therapy.

31. A recombinant protozoan homocysteine desulphurase or functionally active derivative thereof according to claim 27 for use in therapy.

32. A recombinant polypeptide or functionally active derivative thereof according to claim 17 in the manufacture of a medicament for use in therapy.

33. A recombinant polypeptide or functionally active derivative thereof according to claim 17 in the manufacture of a medicament for use in cancer therapy.

34. A pharmaceutical composition comprising a polynucleotide fragment according to claim 17 together with a pharmaceutically acceptable carrier.

35. A pharmaceutical composition comprising a polypeptide or derivative thereof according to claim 27 together with a pharmaceutically acceptable carrier.

36. A recombinant polypeptide or functionally active derivative thereof according to claim 27 to screen for inhibitors thereof.

37. A recombinant polypeptide or functionally active derivative thereof according to claim 27 to remove homocysteine, methionine, or cysteine from a sample.

38. A recombinant polypeptide or functionally active derivative thereof according to claim 27 to determine the presence of enzymes and catalyze reactions involving homocysteine, methionine or cysteine as either substrate or product.

39. A method of assaying homocysteine in a sample, comprising:
(a) contacting said sample with a homocysteine desulphurase enzyme, said homocysteine desulphurase having an amino acid sequence with at least 90% sequence similarity to a sequence selected from the group consisting of SEQ ID NO:2, SEQ ID NO:4, SEQ ID NO:6 and SEQ ID NO:8,
(b) detecting the presence of at least one reaction product formed by the enzyme degradation of any homocysteine in said sample, wherein detection of said reaction product indicates said sample contained homocysteine.

40. The method according to claim 39 wherein said reaction product is selected from the group consisting of α-ketobutyrate, hydrogen sulphide, and ammonia.

41. A kit for diagnostic in vitro determination of a homocysteine level in a sample, wherein the kit comprises:
(a) a homocysteine desulphurase enzyme having an amino acid sequence at least 90% similar to a sequence selected from the group consisting of SEQ ID NO:2, SEQ ID NO:4, SEQ ID NO:6 and SEQ ID NO:8, and
(b) reagents to detect a reaction product formed by enzymatic degradation of homocysteine by said enzyme, said reaction product selected from the group consisting of α-ketobutyrate, hydrogen sulphide, and ammonia.

42. An isolated polynucleotide molecule encoding a protein having an amino acid sequence with at least 90% sequence similarity to a sequence selected from the group consisting of SEQ ID NO:1, SEQ ID NO:3, SEQ ID NO:5 and SEQ ID NO:7, and wherein said protein has homocysteine desulphurase activity.

43. A method of assaying homocysteine in a sample comprising the steps of:
a) contacting the sample with an enzyme that catalyses the degradation of homocysteine, and
b) determining any reaction product(s) formed by enzyme degradation of homocysteine by said enzyme.

44. A method of assaying homocysteine according to claim 39 wherein the enzyme is homocysteine desulphurase.

45. A method of assaying homocysteine according to claim 40 wherein the homocysteine desulphurase is a recombinant protozoan homocysteine desulphurase or functionally active derivative thereof displaying homocysteine desulphurase activity.

46. A method of assaying homocysteine according to claim 41 wherein the recombinant protozoan homocysteine desulphurase is a homocysteine desulphurase substantially as shown in SEQ. ID No: 2, SEQ ID. No:4, SEQ ID No:6 or SEQ. ID No:8.

47. A method of assaying homocysteine according to any one of claims 39 to 4 wherein one of said reaction product(s) is α-ketobutyrate and a level of α-ketobutyrate is determined.

48. A method of assaying homocysteine according to any one of claims 39 to 4 wherein one of said reaction product(s) is hydrogen sulphide and a level of hydrogen sulphide is determined.

49. A method of assaying homocysteine according to any one of claims 39 to 42 wherein on of said reaction(s) is ammonia and a level of ammonia is determined.

50. A method of assaying homocysteine according to claim 43 wherein the level of α-ketobutyrate is determined by reacting the α-ketobutyrate with NADH and lactate dehydrogenase or pyruvate dehydrogenase so as to convert the α-ketobutyrate to a α-hydroxybutyrate with the generation of $NAD^-$ and determining a level of $NAD^+$.

51. A method of assaying homocysteine according to claim 39 wherein said method is sensitive enough to detect a concentration of <5 μmol/l homocysteine.

52. A method of assaying an analyte degradable to homocysteine, which comprises first degrading the analyte to homocysteine and then estimating the homocysteine produced by the method of claim 51.

53. A method according to claim 48 wherein the analyte is homocysteine or methionine.

54. A method of assaying methionine, cysteine or O-acetyl-L-serine in a sample comprising the steps of:
a) contacting the sample with a protozoan homocysteine desulphurase or functionally active derivative thereof capable of degrading methionine, cysteine or O-acetyl-L-serine, and
b) determining any reaction product(s) formed by enzyme degradation of methionine, cysteine or O-acetyl-L-serine.

55. A kit for diagnostic in vitro determination of a homocysteine level in a sample wherein the kit comprises:
a) an enzyme that catalyses the degradation of homocysteine, and
b) means for enabling determination of reaction products produced by degradation of homocysteine by the enzyme.

56. The kit for diagnostic in vitro determination of a homocysteine level in a sample according to claim 55 wherein the enzyme is homocysteine desulphurase.

57. The kit for diagnostic in vitro determination of a homocysteine level in a sample according to claim 56 wherein the homocysteine desulphurase is a recombinant protozoan homocysteine desulphurase or functionally active derivative thereof displaying homocysteine desulphurase activity.

58. The kit for diagnostic in vitro determination of a homocysteine level in a sample according to claim 57 wherein the recombinant protozoan homocysteine desulphurase is a homocysteine desulphurase substantially as shown in SEQ ID No:2, SEQ ID No:4, SEQ ID No:6 or SEQ ID No:8.

59. A polynucleotide fragment encoding a homocysteine desulphurase having at least 80% similarity with the fragment shown in SEQ ID No:1 or SEQ ID No:3.

60. A polynucleotide fragment according to claim 59 wherein said fragment is substantially as shown in SEQ ID No:1 or SEQ ID No:3.

61. A polynucleotide fragment according to either of claims 59 or 60 characterised in that said polynucleotide fragment encodes a polypeptide having an amino acid sequence substantially as shown in SEQ ID No:2, SEQ ID No:4, SEQ ID No:6 or SEQ ID No:8 or a functionally active derivative thereof.

62. A polynucleotide fragment according to claim 59 characterised in that it is a polynucleotide fragment which is substantially the same as a polynucleotide fragment shown in SEQ ID No:1, SEQ ID No:3, SEQ ID No:5 or SEQ ID No:7 or a functionally active derivative thereof.

63. A recombinant nucleic acid molecule comprising a polynucleotide fragment according to claim 59.

64. A recombinant nucleic acid molecule according to claim 59 characterised in that the recombinant nucleic acid molecule comprises regulatory control sequences operably linked to said polynucleotide fragment for controlling expression of said polynucleotide fragment.

65. A recombinant nucleic acid molecule according to claim 59 wherein the recombinant nucleic acid molecule is a plasmid.

66. A recombinant nucleic acid molecule according to claim 64 wherein the recombinant nucleic acid molecule is derived from a viral vector.

67. A prokaryotic host cell transformed by a polynucleotide fragment or recombinant molecule according to any one of claim 63.

68. A recombinant homocysteine desulphurase polypeptide having at least 80% similarity with the polypeptide shown in SEQ ID No:2, SEQ ID No:4, SEQ ID No:6 or SEQ ID No:8 or functionally active derivative thereof.

69. A recombinant homocysteine desulphurase polypeptide according to claim 27 wherein said polypeptide is substantially as shown in SEQ ID No:2, SEQ ID No:4, SEQ ID No:6 or SEQ ID No:8 or functionally active derivative thereof.

70. An antibody immuno-reactive with a polypeptide or fragment according to either of claims 68 and 69.

71. A pharmaceutical composition comprising a polynucleotide fragment according to claim 59 together with a pharmaceutically acceptable carrier.

72. A pharmaceutical composition comprising a polypeptide or derivative thereof according to claim 68 together with a pharmaceutically acceptable carrier.

* * * * *

SEQUENCE LISTING

<160> NUMBER OF SEQ ID NOS: 23

<210> SEQ ID NO 1
<211> LENGTH: 1248
<212> TYPE: DNA
<213> ORGANISM: Trichomonas vaginalis
<220> FEATURE:
<221> NAME/KEY: CDS
<222> LOCATION: (14)..(1201)

<400> SEQUENCE: 1

```
atttttagac aac atg tct cac gag aga atg acc cca gca aca gca tgc        49
            Met Ser His Glu Arg Met Thr Pro Ala Thr Ala Cys
              1               5                  10 atc cat gct aat cca cag aag gat cag ttt gga gca gcc atc cca cca        97
Ile His Ala Asn Pro Gln Lys Asp Gln Phe Gly Ala Ala Ile Pro Pro
         15                  20                  25 atc tac caa aca tca aca ttc gtt ttc gat aac tgc caa cag ggt gga       145
Ile Tyr Gln Thr Ser Thr Phe Val Phe Asp Asn Cys Gln Gln Gly Gly
     30                  35                  40 aac aga ttc gct ggt cag gaa tcc ggc tac atc tac aca cgt ctc ggc       193
Asn Arg Phe Ala Gly Gln Glu Ser Gly Tyr Ile Tyr Thr Arg Leu Gly
 45                  50                  55                  60 aac cca aca gtt tca aac ctc gaa ggc aag atc gcc ttc ctc gag aaa       241
Asn Pro Thr Val Ser Asn Leu Glu Gly Lys Ile Ala Phe Leu Glu Lys
                 65                  70                  75 aca gaa gca tgc gtt gcc aca tct tct ggc atg ggt gcc att gct gct       289
Thr Glu Ala Cys Val Ala Thr Ser Ser Gly Met Gly Ala Ile Ala Ala
             80                  85                  90 aca gtt ttg aca atc ctc aag gcc gga gat cac tta atc tcc gat gag       337
Thr Val Leu Thr Ile Leu Lys Ala Gly Asp His Leu Ile Ser Asp Glu
         95                 100                 105 tgc ctt tat ggc tgc aca cat gct ctc ttt gag cac gca ttg aca aag       385
Cys Leu Tyr Gly Cys Thr His Ala Leu Phe Glu His Ala Leu Thr Lys
    110                 115                 120 ttc ggc atc cag gtc gac ttc atc aac aca gcc atc cca ggc gag gtc       433
Phe Gly Ile Gln Val Asp Phe Ile Asn Thr Ala Ile Pro Gly Glu Val
125                 130                 135                 140 aag aag cac atg aag cca aac aca aag att gtc tat ttc gag aca cca       481
Lys Lys His Met Lys Pro Asn Thr Lys Ile Val Tyr Phe Glu Thr Pro
                145                 150                 155 gcc aac cca aca ctc aag atc atc gac atg gag cgc gtc tgc aag gac       529
Ala Asn Pro Thr Leu Lys Ile Ile Asp Met Glu Arg Val Cys Lys Asp
            160                 165                 170 gcc cac agc cag gag ggc gtc tta gtt atc gcc gat aac aca ttc tgc       577
Ala His Ser Gln Glu Gly Val Leu Val Ile Ala Asp Asn Thr Phe Cys
        175                 180                 185 tca cca atg atc aca aac cca gtc gac ttt ggc gtc gat gtt gtt gtc       625
Ser Pro Met Ile Thr Asn Pro Val Asp Phe Gly Val Asp Val Val Val
    190                 195                 200 cac tct gca aca aag tac atc aac ggc cac aca gat gtc gtc gct ggc       673
His Ser Ala Thr Lys Tyr Ile Asn Gly His Thr Asp Val Val Ala Gly
205                 210                 215                 220 ctt atc tgt ggc aag gct gac ctc ctt caa cag att cgt atg gtt ggt       721
Leu Ile Cys Gly Lys Ala Asp Leu Leu Gln Gln Ile Arg Met Val Gly
                225                 230                 235 atc aag gat atc aca gga tct gtt atc agc cca cac gac gct tgg ctc       769
Ile Lys Asp Ile Thr Gly Ser Val Ile Ser Pro His Asp Ala Trp Leu
            240                 245                 250
```

```
atc aca cgt ggc ctc tca aca ctc aac atc aga atg aag gct gag agc      817
Ile Thr Arg Gly Leu Ser Thr Leu Asn Ile Arg Met Lys Ala Glu Ser
        255                 260                 265 gag aac gcc atg aag gtc gct gag tac ctc aaa tct cac cca gcc gtt      865
Glu Asn Ala Met Lys Val Ala Glu Tyr Leu Lys Ser His Pro Ala Val
    270                 275                 280 gag aag gtt tac tac cca ggc ttc gag gac cac gag ggc cac gat atc      913
Glu Lys Val Tyr Tyr Pro Gly Phe Glu Asp His Glu Gly His Asp Ile
285                 290                 295                 300 gct aag aag cag atg aga atg tac ggt tca atg atc aca ttc atc ctc      961
Ala Lys Lys Gln Met Arg Met Tyr Gly Ser Met Ile Thr Phe Ile Leu
                305                 310                 315 aag tcc ggc ttc gaa ggc gct aag aag ctc ctc gac aac ctc aag ctt     1009
Lys Ser Gly Phe Glu Gly Ala Lys Lys Leu Leu Asp Asn Leu Lys Leu
            320                 325                 330 atc aca ctt gca gtt tcc ctt ggt ggc tgc gag tcc ctc atc cag cac     1057
Ile Thr Leu Ala Val Ser Leu Gly Gly Cys Glu Ser Leu Ile Gln His
        335                 340                 345 cca gct tca atg act cac gct gtc gtt cca aag gag gag cgt gag gcc     1105
Pro Ala Ser Met Thr His Ala Val Val Pro Lys Glu Glu Arg Glu Ala
    350                 355                 360 gct ggt att aca gat ggc atg atc cgc ctt tct gtc ggt att gaa gat     1153
Ala Gly Ile Thr Asp Gly Met Ile Arg Leu Ser Val Gly Ile Glu Asp
365                 370                 375                 380 gcc gac gaa ctc atc gct gat ttc aaa cag ggc ctt gac gct ctt tta     1201
Ala Asp Glu Leu Ile Ala Asp Phe Lys Gln Gly Leu Asp Ala Leu Leu
                385                 390                 395 taaactctac ttagtttctt gactttaatt aaaaaaaaaa aaaaaaa                 1248

<210> SEQ ID NO 2
<211> LENGTH: 396
<212> TYPE: PRT
<213> ORGANISM: Trichomonas vaginalis

<400> SEQUENCE: 2

Met Ser His Glu Arg Met Thr Pro Ala Thr Ala Cys Ile His Ala Asn
1               5                   10                  15

Pro Gln Lys Asp Gln Phe Gly Ala Ala Ile Pro Ile Tyr Gln Thr
            20                  25                  30

Ser Thr Phe Val Phe Asp Asn Cys Gln Gln Gly Gly Asn Arg Phe Ala
        35                  40                  45

Gly Gln Glu Ser Gly Tyr Ile Tyr Thr Arg Leu Gly Asn Pro Thr Val
    50                  55                  60

Ser Asn Leu Glu Gly Lys Ile Ala Phe Leu Glu Lys Thr Glu Ala Cys
65                  70                  75                  80

Val Ala Thr Ser Ser Gly Met Gly Ala Ile Ala Ala Thr Val Leu Thr
                85                  90                  95

Ile Leu Lys Ala Gly Asp His Leu Ile Ser Asp Glu Cys Leu Tyr Gly
            100                 105                 110

Cys Thr His Ala Leu Phe Glu His Ala Leu Thr Lys Phe Gly Ile Gln
        115                 120                 125

Val Asp Phe Ile Asn Thr Ala Ile Pro Gly Glu Val Lys Lys His Met
    130                 135                 140

Lys Pro Asn Thr Lys Ile Val Tyr Phe Glu Thr Pro Ala Asn Pro Thr
145                 150                 155                 160

Leu Lys Ile Ile Asp Met Glu Arg Val Cys Lys Asp Ala His Ser Gln
                165                 170                 175
```

```
Glu Gly Val Leu Val Ile Ala Asp Asn Thr Phe Cys Ser Pro Met Ile
            180                 185                 190

Thr Asn Pro Val Asp Phe Gly Val Asp Val Val His Ser Ala Thr
        195                 200                 205

Lys Tyr Ile Asn Gly His Thr Asp Val Val Ala Gly Leu Ile Cys Gly
    210                 215                 220

Lys Ala Asp Leu Leu Gln Gln Ile Arg Met Val Gly Ile Lys Asp Ile
225                 230                 235                 240

Thr Gly Ser Val Ile Ser Pro His Asp Ala Trp Leu Ile Thr Arg Gly
                245                 250                 255

Leu Ser Thr Leu Asn Ile Arg Met Lys Ala Glu Ser Glu Asn Ala Met
            260                 265                 270

Lys Val Ala Glu Tyr Leu Lys Ser His Pro Ala Val Glu Lys Val Tyr
        275                 280                 285

Tyr Pro Gly Phe Glu Asp His Glu Gly His Asp Ile Ala Lys Lys Gln
    290                 295                 300

Met Arg Met Tyr Gly Ser Met Ile Thr Phe Ile Leu Lys Ser Gly Phe
305                 310                 315                 320

Glu Gly Ala Lys Lys Leu Leu Asp Asn Leu Lys Leu Ile Thr Leu Ala
                325                 330                 335

Val Ser Leu Gly Gly Cys Glu Ser Leu Ile Gln His Pro Ala Ser Met
            340                 345                 350

Thr His Ala Val Val Pro Lys Glu Glu Arg Glu Ala Ala Gly Ile Thr
        355                 360                 365

Asp Gly Met Ile Arg Leu Ser Val Gly Ile Glu Asp Ala Asp Glu Leu
    370                 375                 380

Ile Ala Asp Phe Lys Gln Gly Leu Asp Ala Leu Leu
385                 390                 395

<210> SEQ ID NO 3
<211> LENGTH: 1305
<212> TYPE: DNA
<213> ORGANISM: Trichomonas vaginalis
<220> FEATURE:
<221> NAME/KEY: CDS
<222> LOCATION: (16)..(1209)

<400> SEQUENCE: 3
gactttatat aaaag atg agt ggc cac gct atc gac cca aca cat aca gac      51
                Met Ser Gly His Ala Ile Asp Pro Thr His Thr Asp
                  1               5                  10 aca ctt tcc atc cac gcc aac cca cag aag gat cag ttc ggt gct att      99
Thr Leu Ser Ile His Ala Asn Pro Gln Lys Asp Gln Phe Gly Ala Ile
        15                  20                  25 gtt gct cca atc tac caa aca tcc acc ttc ctc ttc gac aac tgc gac     147
Val Ala Pro Ile Tyr Gln Thr Ser Thr Phe Leu Phe Asp Asn Cys Asp
    30                  35                  40 cag ggt ggt gct cgt ttc ggt ggc aag gaa gcc ggt tac atg tac aca     195
Gln Gly Gly Ala Arg Phe Gly Gly Lys Glu Ala Gly Tyr Met Tyr Thr
45                  50                  55                  60 cgt atc ggt aac cca aca aac tcc gca ctc gaa ggc aag atc gcc aag     243
Arg Ile Gly Asn Pro Thr Asn Ser Ala Leu Glu Gly Lys Ile Ala Lys
                65                  70                  75 ctc gaa cac gct gag gca tgc gct gcc aca gct tct ggc atg ggt gct     291
Leu Glu His Ala Glu Ala Cys Ala Ala Thr Ala Ser Gly Met Gly Ala
            80                  85                  90 att gct gct tct gtc tgg aca ttc ctc aag gcc ggt gat cac ctt atc     339
```

```
Ile Ala Ala Ser Val Trp Thr Phe Leu Lys Ala Gly Asp His Leu Ile
         95                 100                 105 tcc gac gat tgc ctt tat ggc tgc aca cac gcc ctc ttc gag cat cag      387
Ser Asp Asp Cys Leu Tyr Gly Cys Thr His Ala Leu Phe Glu His Gln
        110                 115                 120 ctc cgc aag ttc ggc gtt gaa gtt gat ttc atc gac atg gct gtc cca      435
Leu Arg Lys Phe Gly Val Glu Val Asp Phe Ile Asp Met Ala Val Pro
125                 130                 135                 140 gga aac att gag aag cac ttg aag cca aac aca aga atc gtc tac ttc      483
Gly Asn Ile Glu Lys His Leu Lys Pro Asn Thr Arg Ile Val Tyr Phe
                145                 150                 155 gaa aca cca gct aac cca aca tta aag gtt atc gac atc gaa gac gcc      531
Glu Thr Pro Ala Asn Pro Thr Leu Lys Val Ile Asp Ile Glu Asp Ala
                160                 165                 170 gtc aag cag gcc aga aag cag aag gat atc ctc gtt atc gtt gat aac      579
Val Lys Gln Ala Arg Lys Gln Lys Asp Ile Leu Val Ile Val Asp Asn
        175                 180                 185 acc ttc gct tca cca att ctt aca aac cca ctc gac ctc ggt gtt gat      627
Thr Phe Ala Ser Pro Ile Leu Thr Asn Pro Leu Asp Leu Gly Val Asp
        190                 195                 200 atc gtc gtt cac tcc gct act aag tac atc aat ggc cac acc gat gtt      675
Ile Val Val His Ser Ala Thr Lys Tyr Ile Asn Gly His Thr Asp Val
205                 210                 215                 220 gtc gcc ggc ctt gtc tgc tca aga gct gac atc atc gct aag gtc aag      723
Val Ala Gly Leu Val Cys Ser Arg Ala Asp Ile Ile Ala Lys Val Lys
                225                 230                 235 tcc cag ggt atc aag gat atc aca ggc gcc atc att tcc cca cac gac      771
Ser Gln Gly Ile Lys Asp Ile Thr Gly Ala Ile Ile Ser Pro His Asp
                240                 245                 250 gct tgg ctc atc aca aga ggc aca ctt aca ctc gat atg cgt gtc aag      819
Ala Trp Leu Ile Thr Arg Gly Thr Leu Thr Leu Asp Met Arg Val Lys
        255                 260                 265 cgc gct gcc gag aac gct cag aag gtc gct gaa ttc ctc cat gag cac      867
Arg Ala Ala Glu Asn Ala Gln Lys Val Ala Glu Phe Leu His Glu His
        270                 275                 280 aag gcc gtc aag aag gtc tac tac cca ggc ctt cca gac cat cca ggc      915
Lys Ala Val Lys Lys Val Tyr Tyr Pro Gly Leu Pro Asp His Pro Gly
285                 290                 295                 300 cac gaa atc gcc aag aag cag atg aag atg ttc ggc tct atg atc gca      963
His Glu Ile Ala Lys Lys Gln Met Lys Met Phe Gly Ser Met Ile Ala
                305                 310                 315 ttc gat gtc gac gga tta gag aag gcc aag aaa gtc ctt gac aac tgc     1011
Phe Asp Val Asp Gly Leu Glu Lys Ala Lys Lys Val Leu Asp Asn Cys
                320                 325                 330 cac gtt gtt tct ctc gcc gtt tcc ctc ggt ggt cca gaa tcc ctc atc     1059
His Val Val Ser Leu Ala Val Ser Leu Gly Gly Pro Glu Ser Leu Ile
        335                 340                 345 cag cac cca gct tca atg aca cac gct ggt gtt cca aag gag gaa cgc     1107
Gln His Pro Ala Ser Met Thr His Ala Gly Val Pro Lys Glu Glu Arg
350                 355                 360 gag gct gct ggc cta aca gat aac ctc atc cgc ctc tct gtt ggc tgt     1155
Glu Ala Ala Gly Leu Thr Asp Asn Leu Ile Arg Leu Ser Val Gly Cys
365                 370                 375                 380 gag aac gtt cag gat atc atc gac gac ctc aag cag gct ctc gac tta     1203
Glu Asn Val Gln Asp Ile Ile Asp Asp Leu Lys Gln Ala Leu Asp Leu
                385                 390                 395 gtc ctc taaattaac tttcgaattt cagtaataaa atcctagata tcttcccccc       1259
Val Leu ccaaaaaaaa aaaaaaaaaa aaaaaaaaaa aaaaaaaaaa aaaaaa                  1305
```

```
<210> SEQ ID NO 4
<211> LENGTH: 398
<212> TYPE: PRT
<213> ORGANISM: Trichomonas vaginalis

<400> SEQUENCE: 4

Met Ser Gly His Ala Ile Asp Pro Thr His Thr Asp Thr Leu Ser Ile
1               5                   10                  15

His Ala Asn Pro Gln Lys Asp Gln Phe Gly Ala Ile Val Ala Pro Ile
            20                  25                  30

Tyr Gln Thr Ser Thr Phe Leu Phe Asp Asn Cys Asp Gln Gly Gly Ala
        35                  40                  45

Arg Phe Gly Gly Lys Glu Ala Gly Tyr Met Tyr Thr Arg Ile Gly Asn
    50                  55                  60

Pro Thr Asn Ser Ala Leu Glu Gly Lys Ile Ala Lys Leu Glu His Ala
65                  70                  75                  80

Glu Ala Cys Ala Ala Thr Ala Ser Gly Met Gly Ala Ile Ala Ala Ser
                85                  90                  95

Val Trp Thr Phe Leu Lys Ala Gly Asp His Leu Ile Ser Asp Asp Cys
            100                 105                 110

Leu Tyr Gly Cys Thr His Ala Leu Phe Glu His Gln Leu Arg Lys Phe
        115                 120                 125

Gly Val Glu Val Asp Phe Ile Asp Met Ala Val Pro Gly Asn Ile Glu
    130                 135                 140

Lys His Leu Lys Pro Asn Thr Arg Ile Val Tyr Phe Glu Thr Pro Ala
145                 150                 155                 160

Asn Pro Thr Leu Lys Val Asp Ile Glu Asp Ala Val Lys Gln Ala
                165                 170                 175

Arg Lys Gln Lys Asp Ile Leu Val Ile Val Asp Asn Thr Phe Ala Ser
            180                 185                 190

Pro Ile Leu Thr Asn Pro Leu Asp Leu Gly Val Asp Ile Val Val His
        195                 200                 205

Ser Ala Thr Lys Tyr Ile Asn Gly His Thr Asp Val Val Ala Gly Leu
    210                 215                 220

Val Cys Ser Arg Ala Asp Ile Ile Ala Lys Val Lys Ser Gln Gly Ile
225                 230                 235                 240

Lys Asp Ile Thr Gly Ala Ile Ile Ser Pro His Asp Ala Trp Leu Ile
                245                 250                 255

Thr Arg Gly Thr Leu Thr Leu Asp Met Arg Val Lys Arg Ala Ala Glu
            260                 265                 270

Asn Ala Gln Lys Val Ala Glu Phe Leu His Glu His Lys Ala Val Lys
        275                 280                 285

Lys Val Tyr Tyr Pro Gly Leu Pro Asp His Pro Gly His Glu Ile Ala
    290                 295                 300

Lys Lys Gln Met Lys Met Phe Gly Ser Met Ile Ala Phe Asp Val Asp
305                 310                 315                 320

Gly Leu Glu Lys Ala Lys Lys Val Leu Asp Asn Cys His Val Val Ser
                325                 330                 335

Leu Ala Val Ser Leu Gly Gly Pro Glu Ser Leu Ile Gln His Pro Ala
            340                 345                 350

Ser Met Thr His Ala Gly Val Pro Lys Glu Glu Arg Glu Ala Ala Gly
        355                 360                 365

Leu Thr Asp Asn Leu Ile Arg Leu Ser Val Gly Cys Glu Asn Val Gln
```

```
                    370                 375                 380
Asp Ile Ile Asp Asp Leu Lys Gln Ala Leu Asp Leu Val Leu
385                 390                 395

<210> SEQ ID NO 5
<211> LENGTH: 1248
<212> TYPE: DNA
<213> ORGANISM: Trichomonas vaginalis
<220> FEATURE:
<221> NAME/KEY: CDS
<222> LOCATION: (14)..(1201)

<400> SEQUENCE: 5
atttttagac aac atg tct cac gag aga atg acc cca gca aca gca tgc        49
            Met Ser His Glu Arg Met Thr Pro Ala Thr Ala Cys
            1               5                  10 atc cat gct aat cca cag aag gat cag ttt gga gca gcc atc cca cca       97
Ile His Ala Asn Pro Gln Lys Asp Gln Phe Gly Ala Ala Ile Pro Pro
        15                  20                  25 atc tac caa aca tca aca ttc gtt ttc gat aac tgc caa cag ggt gga      145
Ile Tyr Gln Thr Ser Thr Phe Val Phe Asp Asn Cys Gln Gln Gly Gly
30                  35                  40 aac aga ttc gct ggt cag gaa tcc ggc tac atc tac aca cgt ctc ggc      193
Asn Arg Phe Ala Gly Gln Glu Ser Gly Tyr Ile Tyr Thr Arg Leu Gly
45                  50                  55                  60 aac cca aca gtt tca aac ctc gaa ggc aag atc gcc ttc ctc gag aaa      241
Asn Pro Thr Val Ser Asn Leu Glu Gly Lys Ile Ala Phe Leu Glu Lys
            65                  70                  75 aca gaa gca tgc gtt gcc aca tct tct ggc atg ggt gcc att gct gct      289
Thr Glu Ala Cys Val Ala Thr Ser Ser Gly Met Gly Ala Ile Ala Ala
        80                  85                  90 aca gtt ttg aca atc ctc aag gcc gga gat cac tta atc tcc gat gag      337
Thr Val Leu Thr Ile Leu Lys Ala Gly Asp His Leu Ile Ser Asp Glu
        95                 100                 105 ggc ctt tat ggc tgc aca cat gct ctc ttt gag cac gca ttg aca aag      385
Gly Leu Tyr Gly Cys Thr His Ala Leu Phe Glu His Ala Leu Thr Lys
    110                 115                 120 ttc ggc atc cag gtc gac ttc atc aac aca gcc atc cca ggc gag gtc      433
Phe Gly Ile Gln Val Asp Phe Ile Asn Thr Ala Ile Pro Gly Glu Val
125                 130                 135                 140 aag aag cac atg aag cca aac aca aag att gtc tat ttc gag aca cca      481
Lys Lys His Met Lys Pro Asn Thr Lys Ile Val Tyr Phe Glu Thr Pro
            145                 150                 155 gcc aac cca aca ctc aag atc atc gac atg gag cgc gtc tgc aag gac      529
Ala Asn Pro Thr Leu Lys Ile Ile Asp Met Glu Arg Val Cys Lys Asp
        160                 165                 170 gcc cac agc cag gag ggc gtc tta gtt atc gcc gat aac aca ttc tgc      577
Ala His Ser Gln Glu Gly Val Leu Val Ile Ala Asp Asn Thr Phe Cys
        175                 180                 185 tca cca atg atc aca aac cca gtc gac ttt ggc gtc gat gtt gtt gtc      625
Ser Pro Met Ile Thr Asn Pro Val Asp Phe Gly Val Asp Val Val Val
    190                 195                 200 cac tct gca aca aag tac atc aac ggc cac aca gat gtc gtc gct ggc      673
His Ser Ala Thr Lys Tyr Ile Asn Gly His Thr Asp Val Val Ala Gly
205                 210                 215                 220 ctt atc tgt ggc aag gct gac ctc ctt caa cag att cgt atg gtt ggt      721
Leu Ile Cys Gly Lys Ala Asp Leu Leu Gln Gln Ile Arg Met Val Gly
            225                 230                 235 atc aag gat atc aca gga tct gtt atc agc cca cac gac gct tgg ctc      769
Ile Lys Asp Ile Thr Gly Ser Val Ile Ser Pro His Asp Ala Trp Leu
        240                 245                 250
```

-continued

```
atc aca cgt ggc ctc tca aca ctc aac atc aga atg aag gct gag agc        817
Ile Thr Arg Gly Leu Ser Thr Leu Asn Ile Arg Met Lys Ala Glu Ser
        255                 260                 265 gag aac gcc atg aag gtc gct gag tac ctc aaa tct cac cca gcc gtt        865
Glu Asn Ala Met Lys Val Ala Glu Tyr Leu Lys Ser His Pro Ala Val
270                 275                 280 gag aag gtt tac tac cca ggc ttc gag gac cac gag ggc cac gat atc        913
Glu Lys Val Tyr Tyr Pro Gly Phe Glu Asp His Glu Gly His Asp Ile
285                 290                 295                 300 gct aag aag cag atg aga atg tac ggt tca atg atc aca ttc atc ctc        961
Ala Lys Lys Gln Met Arg Met Tyr Gly Ser Met Ile Thr Phe Ile Leu
                305                 310                 315 aag tcc ggc ttc gaa ggc gct aag aag ctc ctc gac aac ctc aag ctt       1009
Lys Ser Gly Phe Glu Gly Ala Lys Lys Leu Leu Asp Asn Leu Lys Leu
            320                 325                 330 atc aca ctt gca gtt tcc ctt ggt ggc tgc gag tcc ctc atc cag cac       1057
Ile Thr Leu Ala Val Ser Leu Gly Gly Cys Glu Ser Leu Ile Gln His
        335                 340                 345 cca gct tca atg act cac gct gtc gtt cca aag gag gag cgt gag gcc       1105
Pro Ala Ser Met Thr His Ala Val Val Pro Lys Glu Glu Arg Glu Ala
    350                 355                 360 gct ggt att aca gat ggc atg atc cgc ctt tct gtc ggt att gaa gat       1153
Ala Gly Ile Thr Asp Gly Met Ile Arg Leu Ser Val Gly Ile Glu Asp
365                 370                 375                 380 gcc gac gaa ctc atc gct gat ttc aaa cag ggc ctt gac gct ctt tta       1201
Ala Asp Glu Leu Ile Ala Asp Phe Lys Gln Gly Leu Asp Ala Leu Leu
                385                 390                 395 taaactctac ttagtttctt gactttaatt aaaaaaaaaa aaaaaaa                   1248
```

<210> SEQ ID NO 6
<211> LENGTH: 396
<212> TYPE: PRT
<213> ORGANISM: Trichomonas vaginalis

<400> SEQUENCE: 6

```
Met Ser His Glu Arg Met Thr Pro Ala Thr Ala Cys Ile His Ala Asn
1               5                   10                  15

Pro Gln Lys Asp Gln Phe Gly Ala Ala Ile Pro Pro Ile Tyr Gln Thr
            20                  25                  30

Ser Thr Phe Val Phe Asp Asn Cys Gln Gln Gly Gly Asn Arg Phe Ala
        35                  40                  45

Gly Gln Glu Ser Gly Tyr Ile Tyr Thr Arg Leu Gly Asn Pro Thr Val
    50                  55                  60

Ser Asn Leu Glu Gly Lys Ile Ala Phe Leu Glu Lys Thr Glu Ala Cys
65                  70                  75                  80

Val Ala Thr Ser Ser Gly Met Gly Ala Ile Ala Thr Val Leu Thr
                85                  90                  95

Ile Leu Lys Ala Gly Asp His Leu Ile Ser Asp Glu Gly Leu Tyr Gly
                100                 105                 110

Cys Thr His Ala Leu Phe Glu His Ala Leu Thr Lys Phe Gly Ile Gln
            115                 120                 125

Val Asp Phe Ile Asn Thr Ala Ile Pro Gly Glu Val Lys Lys His Met
        130                 135                 140

Lys Pro Asn Thr Lys Ile Val Tyr Phe Glu Thr Pro Ala Asn Pro Thr
145                 150                 155                 160

Leu Lys Ile Ile Asp Met Glu Arg Val Cys Lys Asp Ala His Ser Gln
                165                 170                 175
```

```
Glu Gly Val Leu Val Ile Ala Asp Asn Thr Phe Cys Ser Pro Met Ile
            180                 185                 190

Thr Asn Pro Val Asp Phe Gly Val Asp Val Val His Ser Ala Thr
        195                 200                 205

Lys Tyr Ile Asn Gly His Thr Asp Val Val Ala Gly Leu Ile Cys Gly
    210                 215                 220

Lys Ala Asp Leu Leu Gln Gln Ile Arg Met Val Gly Ile Lys Asp Ile
225                 230                 235                 240

Thr Gly Ser Val Ile Ser Pro His Asp Ala Trp Leu Ile Thr Arg Gly
                245                 250                 255

Leu Ser Thr Leu Asn Ile Arg Met Lys Ala Glu Ser Glu Asn Ala Met
            260                 265                 270

Lys Val Ala Glu Tyr Leu Lys Ser His Pro Ala Val Glu Lys Val Tyr
        275                 280                 285

Tyr Pro Gly Phe Glu Asp His Glu Gly His Asp Ile Ala Lys Lys Gln
    290                 295                 300

Met Arg Met Tyr Gly Ser Met Ile Thr Phe Ile Leu Lys Ser Gly Phe
305                 310                 315                 320

Glu Gly Ala Lys Lys Leu Leu Asp Asn Leu Lys Leu Ile Thr Leu Ala
                325                 330                 335

Val Ser Leu Gly Gly Cys Glu Ser Leu Ile Gln His Pro Ala Ser Met
            340                 345                 350

Thr His Ala Val Val Pro Lys Glu Glu Arg Glu Ala Ala Gly Ile Thr
        355                 360                 365

Asp Gly Met Ile Arg Leu Ser Val Gly Ile Glu Asp Ala Asp Glu Leu
    370                 375                 380

Ile Ala Asp Phe Lys Gln Gly Leu Asp Ala Leu Leu
385                 390                 395

<210> SEQ ID NO 7
<211> LENGTH: 1305
<212> TYPE: DNA
<213> ORGANISM: Trichomonas vaginalis
<220> FEATURE:
<221> NAME/KEY: CDS
<222> LOCATION: (16)..(1209)

<400> SEQUENCE: 7
gactttatat aaaag atg agt ggc cac gct atc gac cca aca cat aca gac      51
                 Met Ser Gly His Ala Ile Asp Pro Thr His Thr Asp
                   1               5                  10 aca ctt tcc atc cac gcc aac cca cag aag gat cag ttc ggt gct att      99
Thr Leu Ser Ile His Ala Asn Pro Gln Lys Asp Gln Phe Gly Ala Ile
         15                  20                  25 gtt gct cca atc tac caa aca tcc acc ttc ctc ttc gac aac tgc gac     147
Val Ala Pro Ile Tyr Gln Thr Ser Thr Phe Leu Phe Asp Asn Cys Asp
     30                  35                  40 cag ggt ggt gct cgt ttc ggt ggc aag gaa gcc ggt tac atg tac aca     195
Gln Gly Gly Ala Arg Phe Gly Gly Lys Glu Ala Gly Tyr Met Tyr Thr
 45                  50                  55                  60 cgt atc ggt aac cca aca aac tcc gca ctc gaa ggc aag atc gcc aag     243
Arg Ile Gly Asn Pro Thr Asn Ser Ala Leu Glu Gly Lys Ile Ala Lys
                 65                  70                  75 ctc gaa cac gct gag gca tgc gct gcc aca gct tct ggc atg ggt gct     291
Leu Glu His Ala Glu Ala Cys Ala Ala Thr Ala Ser Gly Met Gly Ala
             80                  85                  90 att gct gct tct gtc tgg aca ttc ctc aag gcc ggt gat cac ctt atc     339
```

```
Ile Ala Ala Ser Val Trp Thr Phe Leu Lys Ala Gly Asp His Leu Ile
         95                  100                 105 tcc gac gat ggc ctt tat ggc tgc aca cac gcc ctc ttc gag cat cag        387
Ser Asp Asp Gly Leu Tyr Gly Cys Thr His Ala Leu Phe Glu His Gln
    110                 115                 120 ctc cgc aag ttc ggc gtt gaa gtt gat ttc atc gac atg gct gtc cca        435
Leu Arg Lys Phe Gly Val Glu Val Asp Phe Ile Asp Met Ala Val Pro
125                 130                 135                 140 gga aac att gag aag cac ttg aag cca aac aca aga atc gtc tac ttc        483
Gly Asn Ile Glu Lys His Leu Lys Pro Asn Thr Arg Ile Val Tyr Phe
                145                 150                 155 gaa aca cca gct aac cca aca tta aag gtt atc gac atc gaa gac gcc        531
Glu Thr Pro Ala Asn Pro Thr Leu Lys Val Ile Asp Ile Glu Asp Ala
            160                 165                 170 gtc aag cag gcc aga aag cag aag gat atc ctc gtt atc gtt gat aac        579
Val Lys Gln Ala Arg Lys Gln Lys Asp Ile Leu Val Ile Val Asp Asn
        175                 180                 185 acc ttc gct tca cca att ctt aca aac cca ctc gac ctc ggt gtt gat        627
Thr Phe Ala Ser Pro Ile Leu Thr Asn Pro Leu Asp Leu Gly Val Asp
    190                 195                 200 atc gtc gtt cac tcc gct act aag tac atc aat ggc cac acc gat gtt        675
Ile Val Val His Ser Ala Thr Lys Tyr Ile Asn Gly His Thr Asp Val
205                 210                 215                 220 gtc gcc ggc ctt gtc tgc tca aga gct gac atc atc gct aag gtc aag        723
Val Ala Gly Leu Val Cys Ser Arg Ala Asp Ile Ile Ala Lys Val Lys
                225                 230                 235 tcc cag ggt atc aag gat atc aca ggc gcc atc att tcc cca cac gac        771
Ser Gln Gly Ile Lys Asp Ile Thr Gly Ala Ile Ile Ser Pro His Asp
            240                 245                 250 gct tgg ctc atc aca aga ggc aca ctt aca ctc gat atg cgt gtc aag        819
Ala Trp Leu Ile Thr Arg Gly Thr Leu Thr Leu Asp Met Arg Val Lys
        255                 260                 265 cgc gct gcc gag aac gct cag aag gtc gct gaa ttc ctc cat gag cac        867
Arg Ala Ala Glu Asn Ala Gln Lys Val Ala Glu Phe Leu His Glu His
    270                 275                 280 aag gcc gtc aag aag gtc tac tac cca ggc ctt cca gac cat cca ggc        915
Lys Ala Val Lys Lys Val Tyr Tyr Pro Gly Leu Pro Asp His Pro Gly
285                 290                 295                 300 cac gaa atc gcc aag aag cag atg aag atg ttc ggc tct atg atc gca        963
His Glu Ile Ala Lys Lys Gln Met Lys Met Phe Gly Ser Met Ile Ala
                305                 310                 315 ttc gat gtc gac gga tta gag aag gcc aag aaa gtc ctt gac aac tgc       1011
Phe Asp Val Asp Gly Leu Glu Lys Ala Lys Lys Val Leu Asp Asn Cys
            320                 325                 330 cac gtt gtt tct ctc gcc gtt tcc ctc ggt ggt cca gaa tcc ctc atc       1059
His Val Val Ser Leu Ala Val Ser Leu Gly Gly Pro Glu Ser Leu Ile
        335                 340                 345 cag cac cca gct tca atg aca cac gct ggt gtt cca aag gag gaa cgc       1107
Gln His Pro Ala Ser Met Thr His Ala Gly Val Pro Lys Glu Glu Arg
    350                 355                 360 gag gct gct gga cta aca gat aac ctc atc cgc ctc tct gtt ggc tgt       1155
Glu Ala Ala Gly Leu Thr Asp Asn Leu Ile Arg Leu Ser Val Gly Cys
365                 370                 375                 380 gag aac gtt cag gat atc atc gac gac ctc aag cag gct ctc gac tta       1203
Glu Asn Val Gln Asp Ile Ile Asp Asp Leu Lys Gln Ala Leu Asp Leu
                385                 390                 395 gtc ctc taaattttaac tttcgaattt cagtaataaa atcctagata tcttcccccc       1259
Val Leu ccaaaaaaaa aaaaaaaaaa aaaaaaaaaa aaaaaaaaaa aaaaa                     1305
```

<210> SEQ ID NO 8
<211> LENGTH: 398
<212> TYPE: PRT
<213> ORGANISM: Trichomonas vaginalis

<400> SEQUENCE: 8

| Met | Ser | Gly | His | Ala | Ile | Asp | Pro | Thr | His | Thr | Asp | Thr | Leu | Ser | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| His | Ala | Asn | Pro | Gln | Lys | Asp | Gln | Phe | Gly | Ala | Ile | Val | Ala | Pro | Ile |
|     |     |     | 20  |     |     |     |     | 25  |     |     |     |     | 30  |     |     |

| Tyr | Gln | Thr | Ser | Thr | Phe | Leu | Phe | Asp | Asn | Cys | Asp | Gln | Gly | Gly | Ala |
|     |     |     | 35  |     |     |     |     | 40  |     |     |     |     | 45  |     |     |

| Arg | Phe | Gly | Gly | Lys | Glu | Ala | Gly | Tyr | Met | Tyr | Thr | Arg | Ile | Gly | Asn |
|     |     | 50  |     |     |     |     | 55  |     |     |     |     | 60  |     |     |     |

| Pro | Thr | Asn | Ser | Ala | Leu | Glu | Gly | Lys | Ile | Ala | Lys | Leu | Glu | His | Ala |
| 65  |     |     |     |     | 70  |     |     |     |     | 75  |     |     |     |     | 80  |

| Glu | Ala | Cys | Ala | Ala | Thr | Ala | Ser | Gly | Met | Gly | Ala | Ile | Ala | Ala | Ser |
|     |     |     |     | 85  |     |     |     |     | 90  |     |     |     |     | 95  |     |

| Val | Trp | Thr | Phe | Leu | Lys | Ala | Gly | Asp | His | Leu | Ile | Ser | Asp | Asp | Gly |
|     |     |     | 100 |     |     |     |     | 105 |     |     |     |     | 110 |     |     |

| Leu | Tyr | Gly | Cys | Thr | His | Ala | Leu | Phe | Glu | His | Gln | Leu | Arg | Lys | Phe |
|     |     |     | 115 |     |     |     |     | 120 |     |     |     |     | 125 |     |     |

| Gly | Val | Glu | Val | Asp | Phe | Ile | Asp | Met | Ala | Val | Pro | Gly | Asn | Ile | Glu |
|     |     | 130 |     |     |     |     | 135 |     |     |     |     | 140 |     |     |     |

| Lys | His | Leu | Lys | Pro | Asn | Thr | Arg | Ile | Val | Tyr | Phe | Glu | Thr | Pro | Ala |
| 145 |     |     |     |     | 150 |     |     |     |     | 155 |     |     |     |     | 160 |

| Asn | Pro | Thr | Leu | Lys | Val | Ile | Asp | Ile | Glu | Asp | Ala | Val | Lys | Gln | Ala |
|     |     |     |     | 165 |     |     |     |     | 170 |     |     |     |     | 175 |     |

| Arg | Lys | Gln | Lys | Asp | Ile | Leu | Val | Ile | Val | Asp | Asn | Thr | Phe | Ala | Ser |
|     |     |     |     | 180 |     |     |     |     | 185 |     |     |     |     | 190 |     |

| Pro | Ile | Leu | Thr | Asn | Pro | Leu | Asp | Leu | Gly | Val | Asp | Ile | Val | Val | His |
|     |     |     | 195 |     |     |     |     | 200 |     |     |     |     | 205 |     |     |

| Ser | Ala | Thr | Lys | Tyr | Ile | Asn | Gly | His | Thr | Asp | Val | Val | Ala | Gly | Leu |
| 210 |     |     |     |     | 215 |     |     |     |     | 220 |     |     |     |     |     |

| Val | Cys | Ser | Arg | Ala | Asp | Ile | Ile | Ala | Lys | Val | Lys | Ser | Gln | Gly | Ile |
| 225 |     |     |     |     | 230 |     |     |     |     | 235 |     |     |     |     | 240 |

| Lys | Asp | Ile | Thr | Gly | Ala | Ile | Ile | Ser | Pro | His | Asp | Ala | Trp | Leu | Ile |
|     |     |     |     | 245 |     |     |     |     | 250 |     |     |     |     | 255 |     |

| Thr | Arg | Gly | Thr | Leu | Thr | Leu | Asp | Met | Arg | Val | Lys | Arg | Ala | Ala | Glu |
|     |     |     |     | 260 |     |     |     |     | 265 |     |     |     |     | 270 |     |

| Asn | Ala | Gln | Lys | Val | Ala | Glu | Phe | Leu | His | Glu | His | Lys | Ala | Val | Lys |
|     |     |     | 275 |     |     |     |     | 280 |     |     |     |     | 285 |     |     |

| Lys | Val | Tyr | Tyr | Pro | Gly | Leu | Pro | Asp | His | Pro | Gly | His | Glu | Ile | Ala |
|     |     | 290 |     |     |     |     | 295 |     |     |     |     | 300 |     |     |     |

| Lys | Lys | Gln | Met | Lys | Met | Phe | Gly | Ser | Met | Ile | Ala | Phe | Asp | Val | Asp |
| 305 |     |     |     |     | 310 |     |     |     |     | 315 |     |     |     |     | 320 |

| Gly | Leu | Glu | Lys | Ala | Lys | Lys | Val | Leu | Asp | Asn | Cys | His | Val | Val | Ser |
|     |     |     |     | 325 |     |     |     |     | 330 |     |     |     |     | 335 |     |

| Leu | Ala | Val | Ser | Leu | Gly | Gly | Pro | Glu | Ser | Leu | Ile | Gln | His | Pro | Ala |
|     |     |     |     | 340 |     |     |     |     | 345 |     |     |     |     | 350 |     |

| Ser | Met | Thr | His | Ala | Gly | Val | Pro | Lys | Glu | Glu | Arg | Glu | Ala | Ala | Gly |
|     |     |     | 355 |     |     |     |     | 360 |     |     |     |     | 365 |     |     |

Leu Thr Asp Asn Leu Ile Arg Leu Ser Val Gly Cys Glu Asn Val Gln

```
            370             375             380
Asp Ile Ile Asp Asp Leu Lys Gln Ala Leu Asp Leu Val Leu
385                 390                 395
```

<210> SEQ ID NO 9
<211> LENGTH: 28
<212> TYPE: DNA
<213> ORGANISM: Artificial/Unknown
<220> FEATURE:
<221> NAME/KEY: misc_feature
<222> LOCATION: (1)..(28)
<223> OTHER INFORMATION: oligonucleotide primer complementary to
      Trichomonas vaginalis mgl 1

<400> SEQUENCE: 9
tgcctttatg gcggcacaca tgctctct                                     28

<210> SEQ ID NO 10
<211> LENGTH: 27
<212> TYPE: DNA
<213> ORGANISM: Artificial/Unknown
<220> FEATURE:
<221> NAME/KEY: misc_feature
<222> LOCATION: (1)..(27)
<223> OTHER INFORMATION: Oligonucleotide primer complementary to
      Trichomonas vaginalis mgl 2

<400> SEQUENCE: 10
aagagagcat gtgtgccgcc ataaagg                                      27

<210> SEQ ID NO 11
<211> LENGTH: 404
<212> TYPE: PRT
<213> ORGANISM: Homo sapiens

<400> SEQUENCE: 11

```
Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln His Ser Gly Phe Glu Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Thr Val Thr Ile
                85                  90                  95

Thr His Leu Leu Lys Ala Gly Asp Gln Ile Ile Cys Met Asp Asp Val
            100                 105                 110

Tyr Gly Gly Thr Asn Arg Tyr Phe Arg Gln Val Ala Ser Glu Phe Gly
        115                 120                 125

Leu Lys Ile Ser Phe Val Asp Cys Ser Lys Ile Lys Leu Leu Glu Ala
    130                 135                 140

Ala Ile Thr Pro Glu Thr Lys Ile Val Trp Ile Glu Thr Pro Thr Asn
145                 150                 155                 160

Pro Thr Gln Lys Val Ile Asp Ile Glu Gly Cys Ala His Ile Val His
                165                 170                 175

Lys His Gly Asp Ile Ile Leu Val Val Asp Asn Thr Phe Met Ser Pro
            180                 185                 190
```

-continued

```
Tyr Phe Gln Arg Pro Leu Ala Leu Gly Ala Asp Ile Ser Met Tyr Ser
            195                 200                 205

Ala Thr Lys Tyr Met Asn Gly His Ser Asp Val Val Met Gly Leu Val
        210                 215                 220

Ser Val Asn Asp Glu Ser Leu His Asn Arg Leu Arg Phe Leu Gln Asn
225                 230                 235                 240

Ser Leu Gly Ala Val Pro Ser Pro Ile Asp Cys Tyr Leu Cys Asn Arg
                245                 250                 255

Gly Leu Lys Thr Leu His Val Arg Met Glu Lys His Phe Lys Asn Gly
            260                 265                 270

Met Ala Val Ala Gln Phe Leu Glu Ser Asn Pro Trp Val Glu Lys Val
        275                 280                 285

Ile Tyr Pro Gly Leu Pro Ser His Pro Gln His Glu Leu Val Lys Arg
    290                 295                 300

Gln Cys Thr Gly Cys Thr Gly Met Val Thr Phe Tyr Ile Lys Gly Thr
305                 310                 315                 320

Leu Gln His Ala Glu Ile Phe Leu Lys Asn Leu Lys Leu Phe Thr Leu
                325                 330                 335

Ala Glu Ser Leu Gly Gly Phe Glu Ser Leu Ala Glu Leu Pro Ala Ile
            340                 345                 350

Met Thr His Ala Ser Val Leu Lys Asn Asp Arg Asp Val Leu Gly Ile
        355                 360                 365

Ser Asp Thr Leu Ile Arg Leu Ser Val Gly Leu Glu Asp Glu Asp
370                 375                 380

Leu Leu Glu Asp Leu Asp Gln Ala Leu Lys Ala Ala His Pro Pro Ser
385                 390                 395                 400

Gly Ile His Ser

<210> SEQ ID NO 12
<211> LENGTH: 364
<212> TYPE: PRT
<213> ORGANISM: Rattus sp.

<400> SEQUENCE: 12

Cys Cys Gly Ala Ala His Leu Leu Ala Thr Thr Phe Lys Gln Asp Ser
1               5                   10                  15

Pro Gly Gln Ser Ser Gly Phe Val Tyr Ser Arg Ser Gly Asn Pro Thr
            20                  25                  30

Arg Asn Cys Leu Glu Lys Ala Val Ala Ala Leu Asp Gly Ala Lys His
        35                  40                  45

Cys Leu Thr Phe Ala Arg Gly Leu Ala Ala Thr Thr Ile Thr His
    50                  55                  60

Leu Leu Lys Ala Gly Asp Glu Val Ile Cys Met Asp Glu Val Tyr Gly
65                  70                  75                  80

Gly Thr Asn Arg Tyr Phe Arg Arg Val Ala Ser Glu Phe Gly Leu Lys
                85                  90                  95

Ile Ser Phe Val Asp Cys Ser Lys Thr Lys Leu Leu Glu Ala Ala Ile
            100                 105                 110

Thr Pro Gln Thr Lys Ile Val Trp Ile Glu Thr Pro Thr Asn Pro Thr
        115                 120                 125

Leu Lys Leu Ala Asp Ile Lys Ala Cys Ala Gln Ile Val His Lys His
    130                 135                 140

Lys Asp Ile Ile Leu Val Val Asp Asn Thr Phe Met Ser Ala Tyr Phe
145                 150                 155                 160
```

-continued

Gln Arg Pro Leu Ala Leu Gly Ala Asp Ile Cys Met Cys Ser Ala Thr
            165                 170                 175

Lys Tyr Met Asn Gly His Ser Asp Val Val Met Gly Leu Val Ser Val
            180                 185                 190

Asn Ser Asp Asp Leu Asn Glu Arg Leu Arg Phe Leu Gln Asn Ser Leu
            195                 200                 205

Gly Ala Val Pro Ser Pro Phe Asp Cys Tyr Leu Cys Cys Arg Gly Leu
            210                 215                 220

Lys His Cys Arg Ser Gly Trp Arg Asn Thr Phe Gln Asp Gly Met Ala
225                 230                 235                 240

Val Ala Arg Phe Leu Glu Ser Asn Pro Arg Val Glu Lys Val Ile Tyr
            245                 250                 255

Pro Gly Leu Pro Ser His Pro Gln His Glu Leu Ala Lys Arg Ser Ala
            260                 265                 270

Arg Ala Cys Pro Gly Met Val Ser Phe Tyr Ile Lys Gly Thr Leu Gln
            275                 280                 285

His Ala Gln Val Phe Leu Lys Asn Ile Lys Leu Phe Ala Leu Ala Glu
            290                 295                 300

Ser Leu Gly Gly Tyr Glu Ser Leu Ala Glu Leu Pro Ala Ile Met Thr
305                 310                 315                 320

His Ala Ser Val Pro Glu Lys Asp Arg Ala Thr Leu Gly Ile Ser Asp
            325                 330                 335

Thr Leu Ile Arg Leu Ser Val Gly Leu Glu Asp Glu Lys Asp Leu Leu
            340                 345                 350

Glu Asp Leu Gly Gln Ala Leu Lys Ala Ala His Pro
            355                 360

<210> SEQ ID NO 13
<211> LENGTH: 393
<212> TYPE: PRT
<213> ORGANISM: Saccharomyces cerevisiae

<400> SEQUENCE: 13

Met Thr Leu Gln Glu Ser Asp Lys Phe Ala Thr Lys Ala Ile His Ala
1               5                   10                  15

Gly Glu His Val Asp Val His Gly Ser Val Ile Glu Pro Ile Ser Leu
            20                  25                  30

Ser Thr Thr Phe Lys Gln Ser Ser Pro Ala Asn Pro Ile Gly Thr Tyr
            35                  40                  45

Glu Tyr Ser Arg Ser Gln Asn Pro Asn Arg Glu Asn Leu Glu Arg Ala
    50                  55                  60

Val Ala Leu Glu Asn Ala Gln Tyr Gly Leu Ala Phe Ser Ser Gly
65                  70                  75                  80

Ser Ala Thr Thr Ala Thr Ile Leu Gln Ser Leu Pro Gln Gly Ser His
            85                  90                  95

Ala Val Ser Ile Gly Asp Val Tyr Gly Gly Thr His Arg Tyr Phe Thr
            100                 105                 110

Lys Val Ala Asn Ala His Gly Val Glu Thr Ser Phe Thr Asn Asp Leu
            115                 120                 125

Leu Asn Asp Leu Pro Gln Leu Ile Lys Glu Asn Thr Lys Leu Val Trp
            130                 135                 140

Ile Glu Thr Pro Thr Asn Pro Thr Leu Lys Val Thr Asp Ile Gln Lys
145                 150                 155                 160

Val Ala Asp Leu Ile Lys Lys His Ala Ala Gly Gln Asp Val Ile Leu
            165                 170                 175

```
Val Val Asp Asn Thr Phe Leu Ser Pro Tyr Ile Ser Asn Pro Leu Asn
        180                 185                 190

Phe Gly Ala Asp Ile Val Val His Ser Ala Thr Lys Tyr Ile Asn Gly
        195                 200                 205

His Ser Asp Val Val Leu Gly Val Leu Ala Thr Asn Asn Lys Pro Leu
    210                 215                 220

Tyr Glu Arg Leu Gln Phe Leu Gln Asn Ala Ile Gly Ala Ile Pro Ser
225                 230                 235                 240

Pro Phe Asp Ala Trp Leu Thr His Arg Gly Leu Lys Thr Leu His Leu
                245                 250                 255

Arg Val Arg Gln Ala Ala Leu Ser Ala Asn Lys Ile Ala Glu Phe Leu
            260                 265                 270

Ala Ala Asp Lys Glu Asn Val Val Ala Val Asn Tyr Pro Gly Leu Lys
        275                 280                 285

Thr His Pro Asn Asp Val Val Leu Lys Gln His Arg Asp Ala Leu Gly
    290                 295                 300

Gly Gly Met Ile Ser Phe Arg Ile Lys Gly Gly Ala Glu Ala Ala Ser
305                 310                 315                 320

Lys Phe Ala Ser Ser Thr Arg Leu Phe Thr Leu Ala Glu Ser Leu Gly
                325                 330                 335

Gly Ile Glu Ser Leu Leu Glu Val Pro Ala Val Met Thr His Gly Gly
            340                 345                 350

Ile Pro Lys Glu Ala Arg Glu Ala Ser Gly Val Phe Asp Asp Leu Val
        355                 360                 365

Arg Ile Ser Val Gly Ile Glu Asp Thr Asp Asp Leu Leu Glu Asp Ile
370                 375                 380

Lys Gln Ala Leu Lys Gln Ala Thr Asn
385                 390

<210> SEQ ID NO 14
<211> LENGTH: 31
<212> TYPE: DNA
<213> ORGANISM: Artificial/Unknown
<220> FEATURE:
<221> NAME/KEY: modified_base
<222> LOCATION: (11)..(11)
<223> OTHER INFORMATION: i
<221> NAME/KEY: modified_base
<222> LOCATION: (23)..(23)
<223> OTHER INFORMATION: i
<221> NAME/KEY: modified_base
<222> LOCATION: (26)..(26)
<223> OTHER INFORMATION: i
<221> NAME/KEY: misc_feature
<222> LOCATION: (1)..(31)
<223> OTHER INFORMATION: oligonucleotide primer based on cystathionine
      y-lyase

<400> SEQUENCE: 14
gcaagcttgt ntggattgag acnccnacga a                              31

<210> SEQ ID NO 15
<211> LENGTH: 31
<212> TYPE: DNA
<213> ORGANISM: Artificial/Unknown
<220> FEATURE:
<221> NAME/KEY: modified_base
<222> LOCATION: (11)..(11)
<223> OTHER INFORMATION: i
<221> NAME/KEY: misc_feature
<222> LOCATION: (1)..(31)
<223> OTHER INFORMATION: oligonucleotide primer based on cystathionine
```

```
      γ-lyase
<221> NAME/KEY: modified_base
<222> LOCATION: (23)..(23)
<223> OTHER INFORMATION: i
<221> NAME/KEY: modified_base
<222> LOCATION: (26)..(26)
<223> OTHER INFORMATION: i

<400> SEQUENCE: 15
gcaagcttgt ntggatcgag acnccnacaa a                                31

<210> SEQ ID NO 16
<211> LENGTH: 31
<212> TYPE: DNA
<213> ORGANISM: Artificial/Unknown
<220> FEATURE:
<221> NAME/KEY: modified_base
<222> LOCATION: (11)..(11)
<223> OTHER INFORMATION: i
<221> NAME/KEY: modified_base
<222> LOCATION: (23)..(23)
<223> OTHER INFORMATION: i
<221> NAME/KEY: modified_base
<222> LOCATION: (26)..(26)
<223> OTHER INFORMATION: i
<221> NAME/KEY: misc_feature
<222> LOCATION: (1)..(31)
<223> OTHER INFORMATION: oligonucleotide primer based on cystathionine
      γ-lyase

<400> SEQUENCE: 16
gcaagcttgt ntggatagag acnccnacta a                                31

<210> SEQ ID NO 17
<211> LENGTH: 31
<212> TYPE: DNA
<213> ORGANISM: Artificial/Unknown
<220> FEATURE:
<221> NAME/KEY: modified_base
<222> LOCATION: (11)..(11)
<223> OTHER INFORMATION: i
<221> NAME/KEY: modified_base
<222> LOCATION: (23)..(23)
<223> OTHER INFORMATION: i
<221> NAME/KEY: modified_base
<222> LOCATION: (26)..(26)
<223> OTHER INFORMATION: i
<221> NAME/KEY: misc_feature
<222> LOCATION: (1)..(31)
<223> OTHER INFORMATION: oligonucleotide primer based on cystathionine
      γ-lyase

<400> SEQUENCE: 17
gcaagcttgt ntggattgag acnccnacca a                                31

<210> SEQ ID NO 18
<211> LENGTH: 28
<212> TYPE: DNA
<213> ORGANISM: Artificial/Unknown
<220> FEATURE:
<221> NAME/KEY: modified_base
<222> LOCATION: (14)..(14)
<223> OTHER INFORMATION: i
<221> NAME/KEY: modified_base
<222> LOCATION: (23)..(23)
<223> OTHER INFORMATION: i
<221> NAME/KEY: misc_feature
<222> LOCATION: (1)..(28)
<223> OTHER INFORMATION: oligonucleotide primer based on cystathionine
      γ-lyase

<400> SEQUENCE: 18
```
gcctcgagcc gttnatgtac ttngtagc                                                28

<210> SEQ ID NO 19
<211> LENGTH: 28
<212> TYPE: DNA
<213> ORGANISM: Artificial/Unknown
<220> FEATURE:
<221> NAME/KEY: modified_base
<222> LOCATION: (14)..(14)
<223> OTHER INFORMATION: i
<221> NAME/KEY: modified_base
<222> LOCATION: (23)..(23)
<223> OTHER INFORMATION: i
<221> NAME/KEY: misc_feature
<222> LOCATION: (1)..(28)
<223> OTHER INFORMATION: oligonucleotide primer based on cystathionine
      y-lyase

<400> SEQUENCE: 19
gcctcgagcc gttnatatat ttngtggc                                                28

<210> SEQ ID NO 20
<211> LENGTH: 28
<212> TYPE: DNA
<213> ORGANISM: Artificial/Unknown
<220> FEATURE:
<221> NAME/KEY: modified_base
<222> LOCATION: (14)..(14)
<223> OTHER INFORMATION: i
<221> NAME/KEY: modified_base
<222> LOCATION: (23)..(23)
<223> OTHER INFORMATION: i
<221> NAME/KEY: misc_feature
<222> LOCATION: (1)..(28)
<223> OTHER INFORMATION: oligonucleotide primer based on cystathionine
      y-lyase

<400> SEQUENCE: 20
gcctcgagcc gttnatgtac ttngtcgc                                                28

<210> SEQ ID NO 21
<211> LENGTH: 28
<212> TYPE: DNA
<213> ORGANISM: Artificial/Unknown
<220> FEATURE:
<221> NAME/KEY: modified_base
<222> LOCATION: (14)..(14)
<223> OTHER INFORMATION: i
<221> NAME/KEY: modified_base
<222> LOCATION: (23)..(23)
<223> OTHER INFORMATION: i
<221> NAME/KEY: misc_feature
<222> LOCATION: (1)..(28)
<223> OTHER INFORMATION: oligonucleotide primer based on cystathionine
      y-lyase

<400> SEQUENCE: 21
gcctcgagcc gttnatgtac ttngttgc                                                28

<210> SEQ ID NO 22
<211> LENGTH: 24
<212> TYPE: DNA
<213> ORGANISM: Artificial/Unknown
<220> FEATURE:
<221> NAME/KEY: misc_feature
<222> LOCATION: (1)..(24)
<223> OTHER INFORMATION: oligonucleotide primer  based on mgl1 cDNA
      sequence

<400> SEQUENCE: 22
cgccatggct cacgagagaa tgac                                                    24

```
<210> SEQ ID NO 23
<211> LENGTH: 27
<212> TYPE: DNA
<213> ORGANISM: Artificial/Unknown
<220> FEATURE:
<221> NAME/KEY: misc_feature
<222> LOCATION: (1)..(27)
<223> OTHER INFORMATION: oligonucleotide primer based on mgl1 cDNA
      sequence

<400> SEQUENCE: 23
gcagatctta aaagagcgtc aaggccc                                          27
```